United States Patent
Shim

(10) Patent No.: US 10,292,749 B2
(45) Date of Patent: May 21, 2019

(54) CARTRIDGE FOR MIXING AND INJECTING BONE CEMENT, AND BONE CEMENT MIXING AND TRANSFERRING SYSTEM INCLUDING SAME

(71) Applicant: INJECTA INC., Gyeonggi-do (KR)

(72) Inventor: Jae Bum Shim, Gyeonggi-do (KR)

(73) Assignee: INJECTA INC., Gyeonggi-Do (KR)

(*) Notice: Subject to any disclaimer, the term of this patent is extended or adjusted under 35 U.S.C. 154(b) by 242 days.

(21) Appl. No.: 15/316,712

(22) PCT Filed: May 28, 2015

(86) PCT No.: PCT/KR2015/005351
§ 371 (c)(1),
(2) Date: Dec. 6, 2016

(87) PCT Pub. No.: WO2015/199336
PCT Pub. Date: Dec. 30, 2015

(65) Prior Publication Data
US 2017/0143397 A1    May 25, 2017

(30) Foreign Application Priority Data
Jun. 23, 2014  (KR) .................. 10-2014-0076486

(51) Int. Cl.
*A61B 17/88* (2006.01)
*A61M 5/14* (2006.01)
(Continued)

(52) U.S. Cl.
CPC .......... *A61B 17/8833* (2013.01); *A61B 17/56* (2013.01); *A61B 17/8819* (2013.01);
(Continued)

(58) Field of Classification Search
CPC . A61B 17/88; A61B 17/8819; A61B 17/8822; A61B 17/8825; A61B 17/8833
See application file for complete search history.

(56) References Cited

U.S. PATENT DOCUMENTS 4,338,925 A    7/1982  Miller
4,546,767 A   10/1985  Smith
(Continued)

FOREIGN PATENT DOCUMENTS

CN   102470037 A    5/2012
CN   203017057 U    6/2013
(Continued)

OTHER PUBLICATIONS

European Search Report dated Jan. 29, 2018 for EP15811931.3 from European patent office in a counterpart European patent application.
(Continued)

*Primary Examiner* — Christopher J Beccia
(74) *Attorney, Agent, or Firm* — The PL Law Group, PLLC

(57) ABSTRACT

A cartridge for mixing and injecting bone cement includes a body including a cylindrical member, a first coupler and a second coupler at a first open end and a second open end of the cylindrical member, respectively, a first opening/closing member detachably coupled with the first coupler, a second opening/closing member detachably coupled with the second coupler, and a mixing ball in an internal space of the body. A bone cement mixing and transferring system includes the cartridge having powder and liquid components of bone cement inserted and mixing the powder and liquid components, an injection tube coupled with the cartridge after removing the first opening/closing member from the cartridge, and a cement gun mounted to a rear side of the second opening/closing member, the cement gun applying (Continued)

pressure for injecting bone cement mixed in the cartridge into an area to be treated via the injection tube.

20 Claims, 19 Drawing Sheets

(51) Int. Cl.
    *A61M 5/145* (2006.01)
    *A61B 17/56* (2006.01)
    *A61M 31/00* (2006.01)
    *B01F 13/00* (2006.01)
    *B01F 15/00* (2006.01)
    *B01F 15/02* (2006.01)

(52) U.S. Cl.
    CPC ...... *A61B 17/8822* (2013.01); *A61B 17/8825* (2013.01); *A61M 5/14* (2013.01); *A61M 5/145* (2013.01); *A61M 31/00* (2013.01); *B01F 13/0052* (2013.01); *B01F 15/00512* (2013.01); *B01F 15/0279* (2013.01); *A61B 2017/8838* (2013.01); *B01F 2215/0029* (2013.01)

(56) References Cited

U.S. PATENT DOCUMENTS

| | | | |
|---|---|---|---|
| 4,671,263 A | 6/1987 | Draenert | |
| 5,893,488 A | 4/1999 | Hoag et al. | |
| 6,547,432 B2* | 4/2003 | Coffeen | A61B 17/8822 366/130 |
| 8,061,887 B2 | 11/2011 | Henniges et al. | |
| 8,641,667 B2* | 2/2014 | Kurek | A61F 2/4601 604/125 |
| 2002/0092871 A1 | 7/2002 | Rickard et al. | |
| 2002/0118595 A1* | 8/2002 | Miller | A61L 24/06 366/130 |
| 2002/0156483 A1 | 10/2002 | Voellmicke et al. | |
| 2004/0267272 A1* | 12/2004 | Henniges | A61B 17/8822 606/93 |
| 2014/0127809 A1 | 5/2014 | Kurek et al. | |

FOREIGN PATENT DOCUMENTS

| | | |
|---|---|---|
| CN | 103201191 A | 7/2013 |
| EP | 1466572 A2 | 10/2004 |
| KR | 10-2012-0054567 A | 5/2012 |
| KR | 10-1275638 B1 | 6/2013 |
| WO | WO99/67015 A1 | 12/1999 |
| WO | 2004-100771 A2 | 11/2004 |

OTHER PUBLICATIONS

Office action dated Jan. 30, 2018 from China Patent Office in a counterpart China Patent Application No. 201580000540.2 (English translation is also submitted herewith.).

International Search Report for PCT/KR2015/005351.

Office action dated Feb. 23, 2015 from Korean Intellectual Property Office in a counterpart Korean Patent Application No. 10-2014-0076486.

* cited by examiner

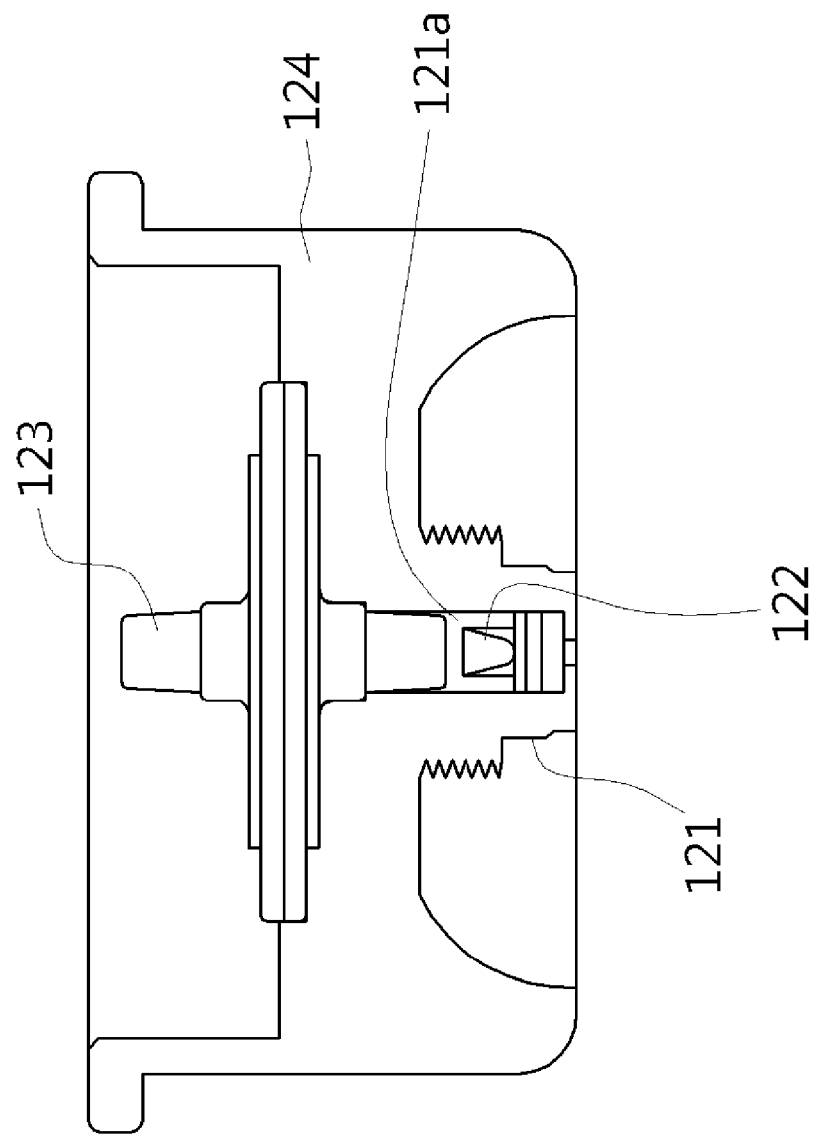

FIG. 6B
120
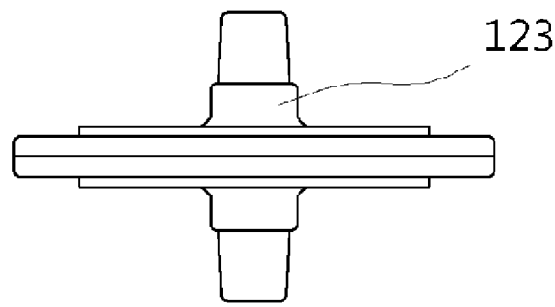
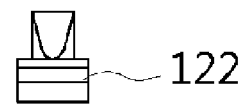
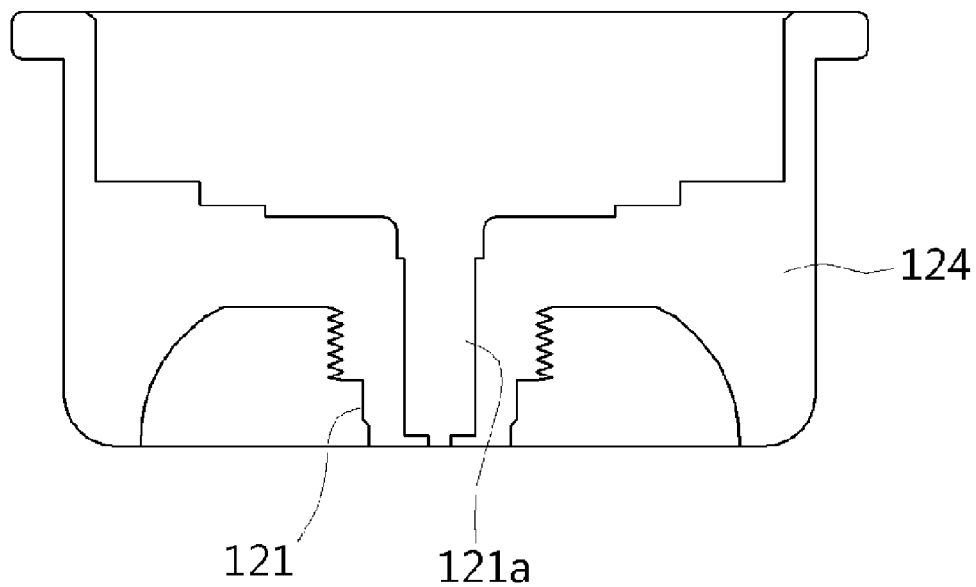

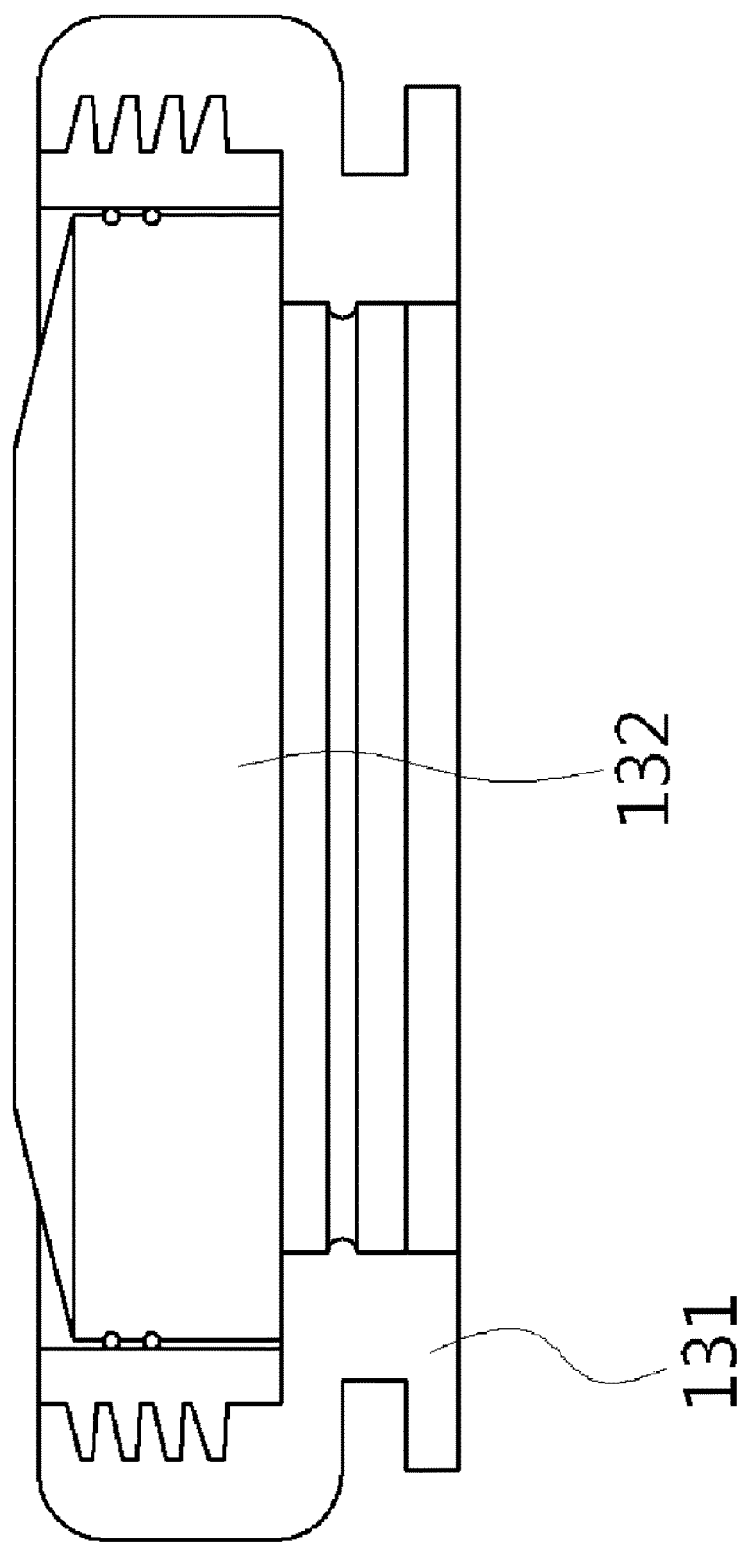

FIG. 7B
130
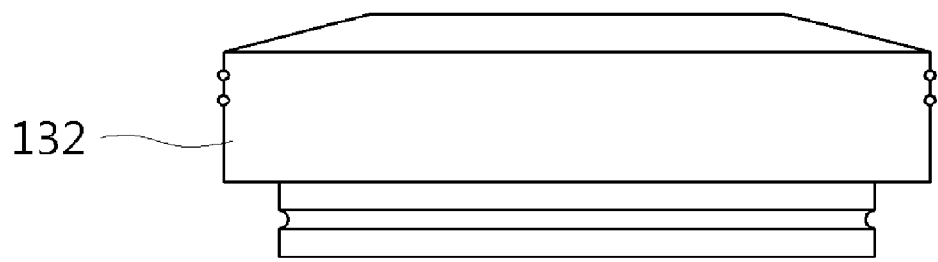
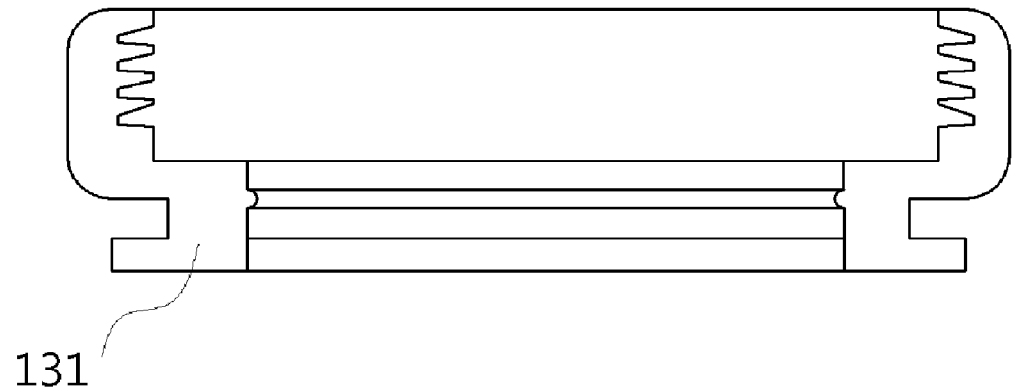

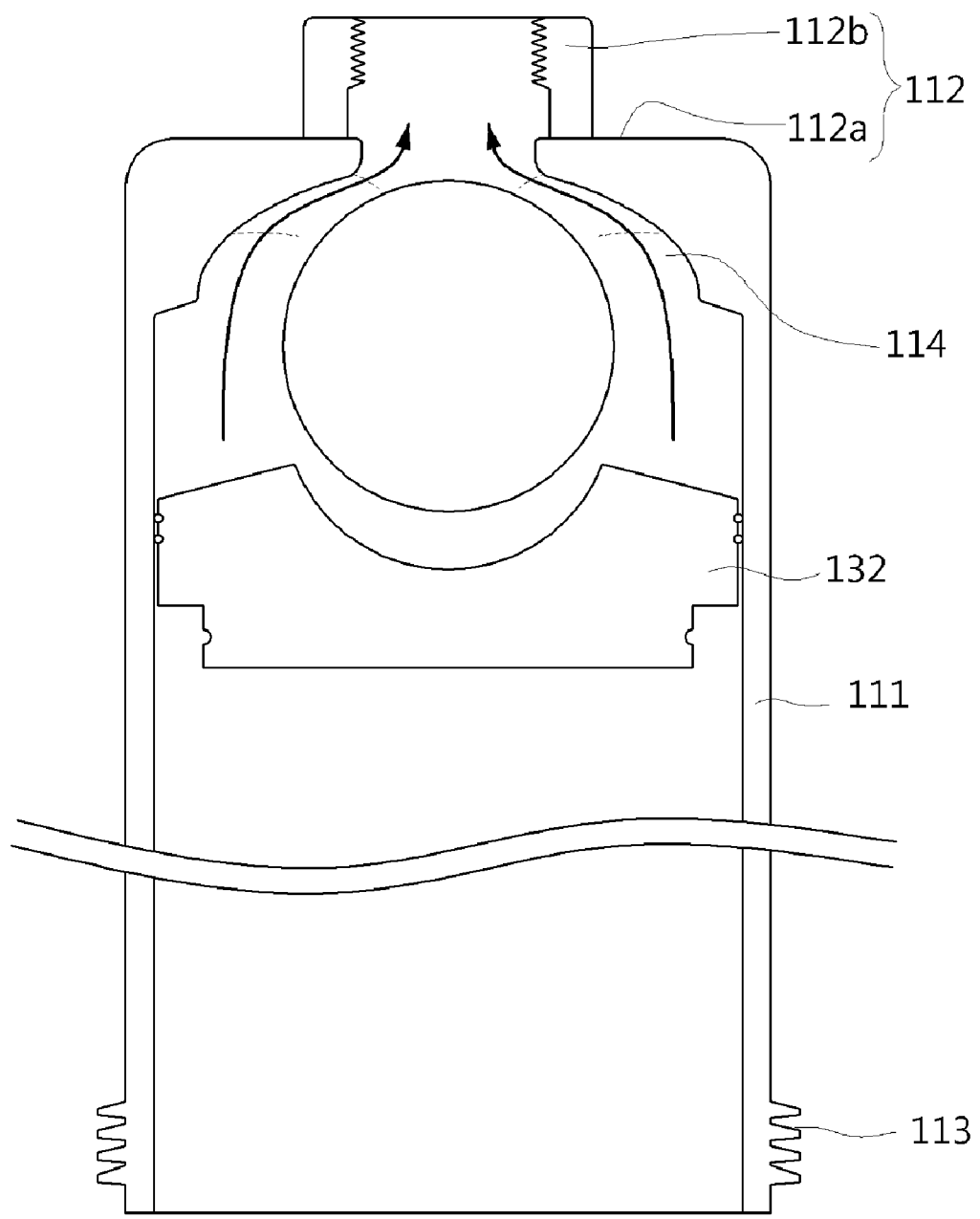

CARTRIDGE FOR MIXING AND INJECTING BONE CEMENT, AND BONE CEMENT MIXING AND TRANSFERRING SYSTEM INCLUDING SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/005351, filed May 28, 2015, which claims priority to the benefit of Korean Patent Application No. 10-2014-0076486 filed in the Korean Intellectual Property Office on Jun. 23, 2014, the entire contents of which are incorporated herein by reference.

TECHNICAL FIELD

The present invention generally relates to a bone cement transferring device. More particularly, the present invention relates to a cartridge for mixing and injecting bone cement, the cartridge having a structure in which a single apparatus can mix and directly inject bone cement, and to a bone cement mixing and transferring system including the same.

BACKGROUND ART

Generally, bone cement is used for filling a free space of a bone and repairing bone defects in an orthopedic surgical procedure. The above-mentioned bone cement is injected into a human body by mixing powder and liquid components to make bone cement while maintaining a viscosity of the bone cement at a predetermined level. To this end, a medical technician manually mixes the powder and liquid components in a mixing container made of an inert material and then inserts the bone cement into a typical syringe, whereby the bone cement can be injected into the human body during surgery.

As such, the medical technician manually mixes the powder and liquid components in the mixing container, so it is difficult to ensure uniformity of distribution under a complicated mixing and transferring system depending on an open and manual process using a bowl or a spatula in the related art. Further, such system is problematic in terms of not only increasing the risk of infection in the area to be treated but also being complicated and time-consuming.

In order to solve the above-described problems, as shown in FIG. 1, Korean Patent No. 1275638 discloses "a bone cement mixing and injecting device 1" including: a cylinder body 10, the cylinder body including a cylindrical lower body part having a space for containing bone cement therein and having threads on an upper side thereof, a piston body reciprocating in the space of the lower body part, and an upper body part having a handle, and being coupled with the lower body part by a screw-type engagement and being coupled with the piston body therein; a mixing member 20 passing through the upper body part, the mixing member pressurizing bone cement to be inserted into the space of the lower body part by reciprocating therein; and an injecting member 30 having a handle on a first side thereof and an injecting rod externally provided with threads corresponding to threads formed inside the upper body part, the injecting member having a diameter larger than a diameter of a mixing rod of the mixing member so the mixing rod passes through the injecting rod.

However, the device disclosed in the Korean Patent is problematic in that it requires much strength for mixing bone cement due to a structure of the mixing member. Another problem of the device resides in that it may not achieve mixing uniformity. Moreover, the injecting member should be additionally inserted into the device for injection, thereby causing inconvenience in use.

Therefore, it is required to develop an improved technology of a bone cement mixing and transferring system.

SUMMURY

As a result of repeated studies, the inventors have completed the present invention by developing a bone cement mixing and injecting cartridge, in which the cartridge can directly inject bone cement after mixing powder and liquid components of the bone cement.

Accordingly, an object of present invention is to propose a bone cement mixing and injecting cartridge and a bone cement mixing and transferring system, in which bone cement can be injected into an area to be treated by using a mixing means that is used for uniformly mixing powder and liquid components of the bone cement without separating the mixing means from the cartridge.

A another object of the present invention is to propose a bone cement mixing and injecting cartridge and a bone cement mixing and transferring system, in which bone cement can be injected into the area to be treated by using an existing cement gun by preparing bone cement in a simple manner unlike a conventional mixing method using an impeller, and in a hygienic manner to minimize the risk of infection.

A further object of the present invention is to propose a bone cement mixing and injecting cartridge and a bone cement mixing and transferring system, the cartridge and system enabling an operator to check viscosity of bone cement during a process of mixing powder and liquid components of bone cement in the cartridge.

Still another object of the present invention is to propose a bone cement mixing and injecting cartridge and a bone cement mixing and transferring system, the cartridge and system not only enabling an operator to perform a procedure in a short time while maintaining a vacuum inside the cartridge, but also enabling the operator to mix powder and liquid components of bone cement while maintaining the vacuum inside the cartridge although a vacuum process is not additionally performed.

Still another object of the present invention is to propose a bone cement mixing and injecting cartridge and a bone cement mixing and transferring system, the cartridge and system enabling preparation of bone cement that is to be injected without impurities into the area by eliminating pieces of glass, etc. that are generated when releasing a glass tube filled with the liquid component when inserting the liquid component into the cartridge, thereby ensuring safety of the cartridge.

The present invention is not limited by the above mentioned object and other unmentioned objects can be clearly understood from the following description by those having ordinary skill in the technical field to which the present invention pertains.

In order to achieve the above object, according to one aspect of the present invention, there is provided a cartridge for mixing and injecting bone cement, the cartridge including: a body including a cylindrical member having a square cross-section in a lengthwise direction thereof, a first coupling means provided in a first open end of the cylindrical member, and a second coupling means provided in a second open end of the cylindrical member; a first opening/closing means detachably coupled with the first coupling means; a second opening/closing means detachably coupled with the second coupling means; and at least one mixing ball provided in an internal space of the body.

In a preferred embodiment, the first coupling means may be provided with a shoulder part provided at a first open end of the cylindrical member, the shoulder part extending therefrom, and a neck part cylindrically protruding at a center of the first open end of the cylindrical member by perpendicularly extending from the shoulder part.

In a preferred embodiment, the first opening/closing means may be provided with a protruding member that is inserted into the first coupling means and is coupled with the first coupling means.

In a preferred embodiment, the second coupling means may be provided with a threaded portion integrally formed on an outer surface of the second open end of the cylindrical member.

In a preferred embodiment, the second opening/closing means may be provided with a cylindrical housing member that surrounds an outer surface of the second coupling means and is coupled with the second coupling means, and a plunger member detachably coupled with a first open end of the cylindrical housing member.

In a preferred embodiment, when the second opening/closing means is coupled with the second coupling means, the cylindrical member may be inserted between the cylindrical housing member and the plunger member.

In a preferred embodiment, a first end of the plunger member may be detachably coupled with the cylindrical housing member, and a second end of the plunger member may be provided with an O-ring.

In a preferred embodiment, the cartridge for mixing and injecting bone cement may further include a maintenance member maintaining a vacuum of the internal space of the body after the internal space of the body is vacuumized.

In a preferred embodiment, the maintenance member may be a check valve provided in the first opening/closing means.

In a preferred embodiment, the cartridge for mixing and injecting bone cement may further include a filter member eliminating odors that are discharged when vacuumizing the internal space of the body of the cartridge.

In a preferred embodiment, the cartridge for mixing and injecting bone cement may further include a mixing ball supporting portion provided inside the first open end of the cylindrical member and the first coupling means.

According to another aspect of the present invention, there is provided a bone cement mixing and transferring system, including: the cartridge of any one of above-described cartridges, the cartridge having powder and liquid components of bone cement inserted into the internal space thereof and mixing the powder and liquid components therein; an injection tube coupled with the cartridge after removing the first opening/closing means from the cartridge; and a cement gun mounted to a rear side of the second opening/closing means of the cartridge, the cement gun applying pressure for injecting bone cement mixed in the cartridge into an area to be treated via the injection tube.

In a preferred embodiment, the bone cement mixing and transferring system may further include a vacuum processing device performing a vacuum process of vacuumizing the internal space of the body of the cartridge.

In a preferred embodiment, the vacuum processing device may be used before mixing the powder and liquid components of bone cement that have been inserted into the internal space of the body of the cartridge.

In a preferred embodiment, the bone cement mixing and transferring system may further include an inserting tool used when inserting the powder and liquid components of bone cement into the internal space of the body of the cartridge.

In a preferred embodiment, the inserting tool may include a filter provided in an end of the inserting tool that comes into contact with the internal space of the body of the cartridge.

In a preferred embodiment, the powder and liquid components of bone cement that have been inserted into the internal space of the body of the cartridge may be mixed therein by shaking the cartridge in lengthwise directions thereof.

The present invention has the following advantages.

First, according to the bone cement mixing and injecting cartridge and the bone cement mixing and transferring system, it is possible to inject bone cement into an area to be treated by using the mixing means that is used for uniformly mixing powder and liquid components of the bone cement, without separating the mixing means from the cartridge.

Further, according to the bone cement mixing and injecting cartridge and the bone cement mixing and transferring system, it is possible to inject bone cement into an area to be treated by using an existing cement gun by preparing bone cement in a simple manner unlike a conventional mixing method using an impeller, and in a hygienic manner, thereby minimizing the risk of infection.

Further, according to the bone cement mixing and injecting cartridge and the bone cement mixing and transferring system, it is possible to enable an operator to check viscosity of bone cement during the process of mixing powder and liquid components of bone cement in the cartridge.

Further, according to the bone cement mixing and injecting cartridge and the bone cement mixing and transferring system, it is possible to not only enable the operator to perform the procedure in a short time while maintaining the vacuum inside the cartridge, but also mix powder and liquid components of bone cement while maintaining the vacuum inside the cartridge although the vacuum process is not additionally performed.

Further, according to the bone cement mixing and injecting cartridge and the bone cement mixing and transferring system, it is possible to prepare bone cement that is to be injected into the area to be treated without impurities by eliminating pieces of glass, etc. that are generated when releasing a glass tube filled with the liquid component of bone cement when inserting the liquid component into the cartridge, thereby ensuring safety of the cartridge.

Effects obtainable from the present invention are not limited by the above mentioned effect and other unmentioned effects can be clearly understood from the following description by those having ordinary skill in the technical field to which the present invention pertains.

BRIEF DESCRIPTION OF THE DRAWING

FIG. 6A is a cross-sectional view illustrating an example of a first opening/closing means provided in the cartridge according to the present invention, and FIG. 6B is an exploded cross-sectional view illustrating the first opening/closing means.

FIG. 7A is a cross-sectional view illustrating an example of a second opening/closing means provided in the cartridge according to the present invention, and FIG. 7B is an exploded cross-sectional view illustrating the second opening/closing means.

FIG. 8 is a schematic cross-sectional view illustrating discharge of bone cement from a body of the cartridge for mixing and injecting bone cement of the present invention, performed by operation of a plunger member without removing a mixing ball from the body of the cartridge.

DETAILED DESCRIPTION

Figure 1:
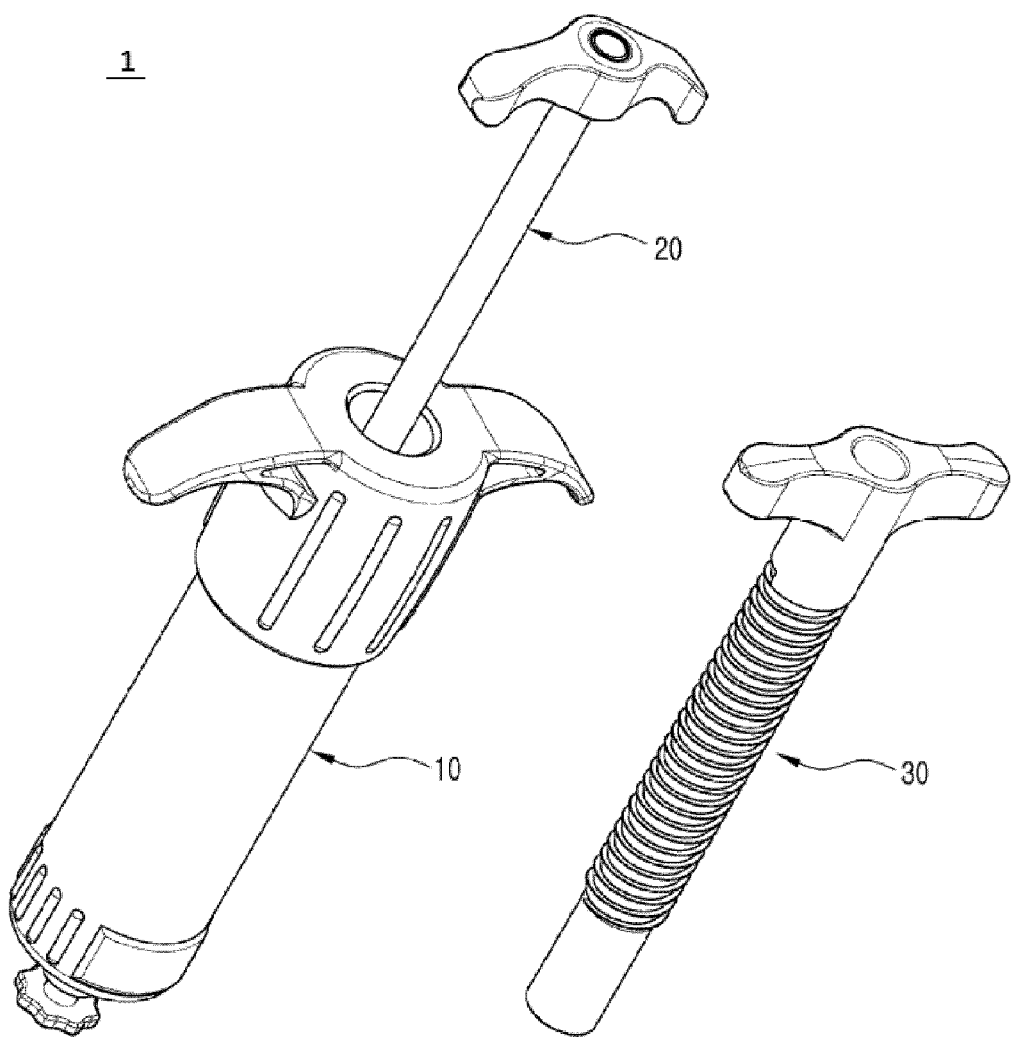
FIG. 1 is a perspective view illustrating a bone cement mixing and injecting apparatus according to the related art.

Although general terms being widely used at present were selected as terminology used in the exemplary embodiments while considering the functions of the exemplary embodiments, they may vary according to intentions of one of ordinary skill in the art, judicial precedents, the advent of new technologies, and the like. Further, terms arbitrarily selected by the applicant may also be used in a specific case. In this case, their meanings can be obtained based on the detailed description of the exemplary embodiments. Hence, the terms must be defined based on the meanings of the terms and the contents of the entire specification, and not by simply stating the terms themselves.

Hereinafter, a technical configuration of the present invention will be described in detail with reference to preferred embodiments illustrated in the accompanying drawings.

However, it should be understood that the present invention is not limited to the following embodiments and may be embodied in different ways. Wherever possible, the same reference numerals will be used throughout the drawings and the description to refer to the same or like parts.

The technical configuration of a cartridge for mixing and injecting bone cement of the present invention is characterized in that it can be used to inject bone cement into an area to be treated by using a mixing means that is used for uniformly mixing powder and liquid components of the bone cement, without separating the mixing means from the cartridge.

In other words, when using an impeller for mixing powder and liquid components of bone cement, it is required to remove the impeller from the cartridge after mixing, thereby complicating a process of preparing bone cement and causing the risk of infection in an area to be treated. Further, when using an apparatus shown in FIG. 1, an existing cement gun cannot be used to inject bone cement, so the apparatus has a complicated structure due to requirement of an additional injecting member.

Accordingly, the cartridge for mixing and injecting bone cement of the present invention includes: a body 110 including a cylindrical member 111 having a square cross-section in a lengthwise direction thereof, a first coupling means 112 provided in a first open end of the cylindrical member 111, and a second coupling means 113 provided in a second open end of the cylindrical member 111; a first opening/closing means 120 detachably coupled with the first coupling means 112; a second opening/closing means 130 detachably coupled with the second coupling means 113; and at least one mixing ball 140 provided in an internal space of the body.

Hereinafter, the cartridge 100 for mixing and injecting bone cement of the present invention will be described in detail with reference to FIGS. 2 to 5 illustrating schematic views of the cartridge 100 for mixing and injecting bone cement according to embodiments of the present invention.

Figure 2:
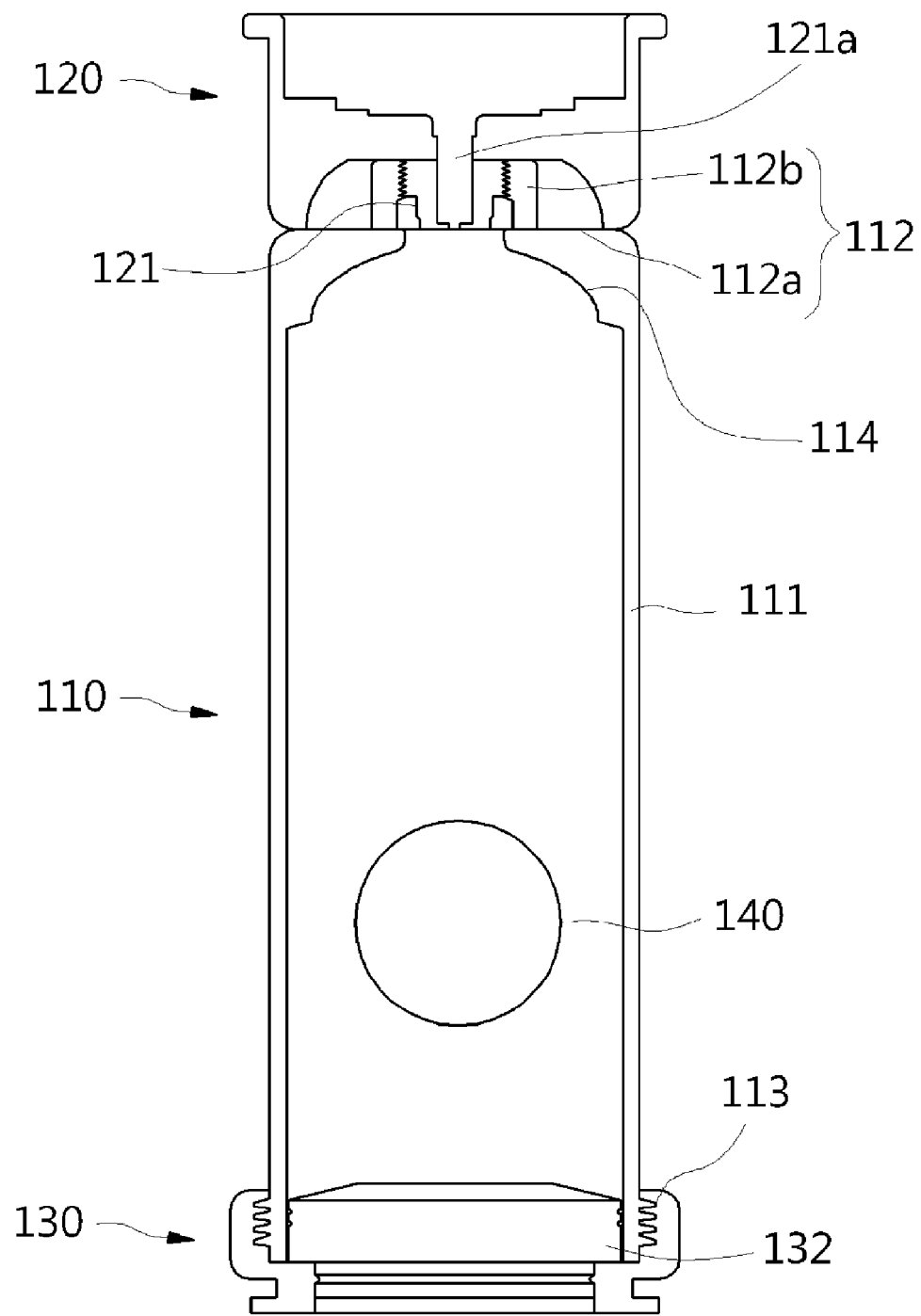
FIG. 2 is a cross-sectional view illustrating a cartridge for mixing and injecting bone cement according to an embodiment of the present invention.

FIG. 2 is a cross-sectional view illustrating a cartridge 100 for mixing and injecting bone cement according to an embodiment of the present invention As shown in FIG. 2, the cartridge 100 for mixing and injecting bone cement of the present invention includes the body 110, the first opening/closing means 120, the second opening/closing means 130, and the mixing ball 140.

The body 110 may be substantially a cylindrical shape and may be provided with an internal space where powder and liquid components of bone cement are uniformly mixed therein. According to the embodiment of the present invention, the body 110 may be provided with the cylindrical member 111, the first coupling means 112, and the second coupling means 113.

The cylindrical member 111 is provided with a substantially cylindrical side wall having a circle or elliptical cross-section in a widthwise direction and having a square cross-section in a lengthwise direction, and the internal space is limited by the side wall. Here, both sides of the internal space are open by both open ends of the cylindrical member 111 are open in the lengthwise direction.

The first coupling means 112 is provided at the first open end of the cylindrical member 111, and plays a role of coupling the first opening/closing means 120 and the body 110 and closing a side of the internal space that is open by the first open end of the cylindrical member 111 out of both sides of the internal space that are open by both open ends of the cylindrical member 111 in the lengthwise direction thereof. Here, a shape of the first coupling means 112 provided in the first open end of the cylindrical member 111 is not limited if it can be coupled with the first opening/closing means 120. However, the shape of the first coupling means 112 may vary while corresponding to a shape of the first opening/closing means 120. As shown in FIG. 2, the first coupling means 112 according to the embodiment of the present invention may be provided with a shoulder part 112a forted at the first open end of the cylindrical member 111 and extending therefrom, and a neck part 112b cylindrically protruding at a center of the first open end of the cylindrical member 111 by perpendicularly extending from the shoulder part 112a. Here, an inner surface of the neck part 112b or an outer surface thereof may be provided with a coupling portion for being coupled with the first opening/closing means 120 or an injection tube 200. According to the embodiment of the present invention, a threaded portion is formed in the inner surface of the neck part 112b.

The second coupling means 113 is provided at the second open end of the cylindrical member 111, and plays a role of coupling the second opening/closing means 130 and the body 110 and closing a side that is open by the second open end of the cylindrical member 111 out of both sides of the internal space that are open by the both open ends of the cylindrical member 111 in the lengthwise direction thereof. Accordingly, a shape of the second coupling means 113 is not limited if it can be provided at the second open end of the cylindrical member 111 and coupled with the second opening/closing means 130. However the shape of the first coupling means 112 may vary to be corresponding to a shape of the second opening/closing means 130. Given that a cement gun 300 is mounted to a rear side of the second opening/closing means 130 coupled with the second coupling means 113, a configuration in which the second opening/closing means 130 is coupled with the second coupling means 113 while surrounding the second open end of the cylindrical member 111 may be proposed. Specifically, as shown in FIG. 2, the second coupling means 113 may be provided with a threaded portion that is integrally formed on an outer surface of the second open end of the cylindrical member 111.

The first opening/closing means 120 is coupled with the first coupling means 112 that is provided in the first open end of the cylindrical member 111 that forms the body 110, and opens or closes the side that is open by the first open end of the cylindrical member 111 out of both sides of the internal space that are open by both open ends of the cylindrical member 111 in the lengthwise direction thereof. Accordingly, a shape of the first opening/closing means 120 is not limited if it can be coupled with the first coupling means 112 of the body 110 so as to be opened and closed. Given that the internal space of the body 110 of the cartridge 100 should be vacuumized, a coupling structure that allows the internal space of the body 110 of the cartridge 100 to be easily vacuum sealed may be desirable.

As shown in FIG. 2, a configuration that includes a protruding member 121 that is inserted into inside the first coupling means 112 and is coupled with the first coupling means 112 may be employed as the embodiment of the first opening/closing means 120.

A coupling portion may be formed on a partial or entire outer surface of the protruding member 121 and may be coupled with the first coupling means 112. As shown in FIG. 2, a threaded portion may be formed in a shape corresponding to the threaded portion formed in the inner surface of the neck part 112b of the first coupling means 112 so as to be coupled with each other.

Further, as shown in FIG. 2, the first opening/closing means 120 comes into contact with the internal space of the body 110 of the cartridge 100 through the protruding member 121. Thus, a through hole 121a may be formed in the protruding member 121 so as to perform a vacuum process with respect to the internal space while maintaining engagement of the first opening/closing means 120 and the first coupling means 112. Here, the internal space of the body 110 of the cartridge 100 may be connected to the outside via the through hole 121a.

Of course, the first opening/closing means 120 may surround the first coupling means 112 rather than being inserted thereto although this is not shown in the drawing.

The second opening/closing means 130 is coupled with the second coupling means 113 formed in the second open end of the cylindrical member 111 that forms the body 110 and opens or closes a side that is open by the second open end of the cylindrical member 111 out of both sides of the internal space that are open by both open ends of the cylindrical member 111 in the lengthwise direction thereof. Accordingly, a shape of the second opening/closing means 130 is not limited if it can be coupled with the second coupling means 113 of the body 110 so as to be opened and closed. Given that the internal space of the body 110 of the cartridge 100 should be vacuum processed and, a coupling structure that allows the internal space to be easily vacuum sealed and allows the cement gun 300 mounted to the rear side of the second opening/closing means 130 to easily inject bone cement by pressurizing a plunger member 132 provided in the second opening/closing means 130 may be desirable.

As shown in FIG. 2, a configuration in which the second opening/closing means 130 is coupled with the second coupling means 113 integrally formed on the outer surface of the second open end of the cylindrical member 111 and surrounds the second open end of the cylindrical member 111 may be proposed as the embodiment of such coupling structure.

Specifically, the second opening/closing means 130 may include a cylindrical housing member 131 that surrounds an outer surface of the second opening/closing means 130 and is coupled with the second coupling means 113, and the plunger member 132 that is detachably coupled with a first open end of the cylindrical housing member 131.

The cylindrical housing member 131 is a cylindrical member of which upper and lower sides are open, in which a coupling portion that is coupled with the second coupling means 113 may be formed on an inner surface of an upper open end that is coupled with the second coupling means 113. As shown in the drawing, a threaded portion may be formed as the coupling portion. In such configuration, when the second opening/closing means 130 is coupled with the second coupling means 113, the cylindrical member 111 is inserted into between the cylindrical housing member 131 and the plunger member 132.

Further, an annular protrusion is formed on an inner surface of a lower open end of the cylindrical housing member 131 so the plunger member 132 may be detachably seated therein. By such configuration, the plunger member 132 is coupled with annular protrusion formed on the inner surface of the lower open end of the cylindrical housing member 131. Thus, the plunger member 132 has fixing strength to resist pressure applied when vacuumizing the internal space of the body 110 of the cartridge 100 and to resist pressure applied by the mixing ball when mixing bone cement. In other words, the fixing strength of the plunger member 132 can hold the plunger member 132 in the cylindrical housing member 131 until predetermined pressure capable of separating the plunger member 132 from the annular protrusion is applied to the plunger member 132 when a piston of the cement gun 300 pushes the plunger member 132.

The mixing ball 140 is disposed in the internal space of the body 110 of the cartridge 100 and functions as a mixing means to mix powder and liquid components of bone cement. The mixing ball 140 may be a sphere having a circle or an elliptical cross section or may be a three-dimensional figure similar to sphere so as to move inside the internal space of the body 110 of the cartridge 100 without interruption. Here, the mixing ball 140 is not allowed to be discharged to the outside of the body 110 of the cartridge 100 while freely moving inside the internal space thereof. To this end, a diameter of the mixing ball 140 may be smaller than a diameter of the cylindrical member 111 and may be larger than a diameter of the neck part 112b. Further, a material of the mixing ball 140 is not limited as long as it is a material that does not cause a chemical reaction with powder and liquid components of bone cement. However, the material of the mixing ball should be suitable for use in a medical procedure or treatment. For example, the mixing ball 140 may be made of metal, ceramic, polymer, etc. having chemical resistance and corrosion resistance. Specifically, the metal may be stainless steel, titanium, etc., the ceramic may be alumina, zirconium, glass, etc., and the polymer may be Teflon.

Figure 3:
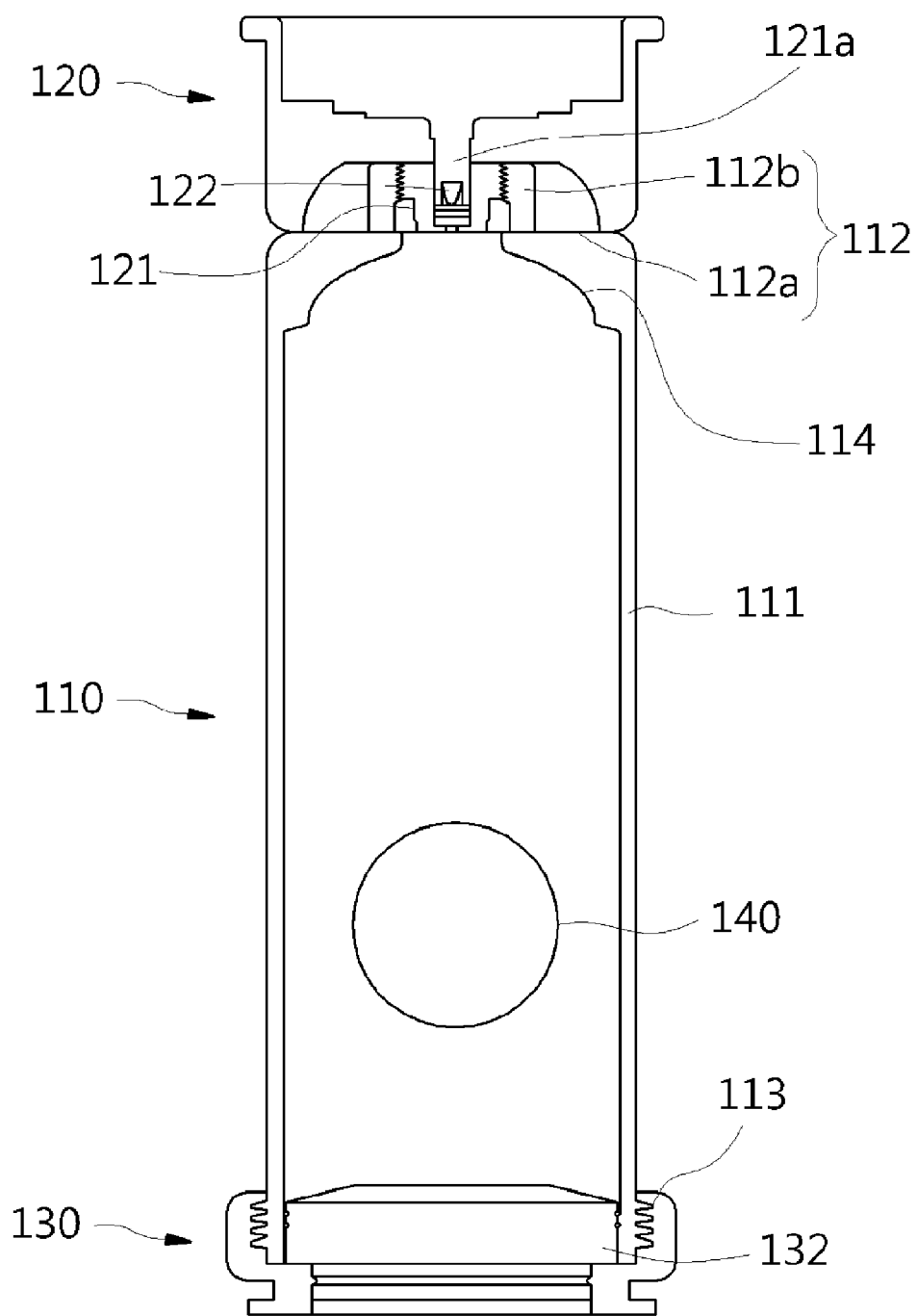
FIG. 3 is a cross-sectional view illustrating a cartridge for mixing and injecting bone cement according to another embodiment of the present invention.

FIG. 3 is a cross-sectional view illustrating a cartridge for mixing and injecting bone cement according to another embodiment of the present invention.

As shown in FIG. 3, the configuration of the cartridge 100 according to this embodiment remains the same as the configuration of the cartridge 100 of FIG. 2 except the structure of the first opening/closing means 120. Thus, the first opening/closing means 120 will be mainly described hereinafter.

Further, the first opening/closing means 120 of the cartridge 100 for mixing and injecting bone cement according to this embodiment of the present invention has the same configuration as the first opening/closing means shown in FIG. 2 except that a maintenance member 122 is further provided. Thus, other elements will refer to the above-mentioned description, so only the maintenance member 122 will be described hereinafter.

The maintenance member 122 is an element for maintaining a vacuum of the internal space of the body 110 of the cartridge 100 after the internal space thereof is vacuumized. Since the powder and liquid components of bone cement are mixed in the internal space of the body 110 of the cartridge 100 by shaking the cartridge 100 in opposite directions without an additional vacuum process, the maintenance member 122 is advantageous in achieving a simple preparation of bone cement. In other words, when mixing the powder and liquid components of bone cement that have been inserted into the cartridge 100, the internal space of the body 110 of the cartridge 100 should maintain a vacuum so as to prevent air bubbles from being generated in bone cement. For example, in the configurations of the conventional cartridge of FIG. 1 and the cartridge of FIG. 2, the internal space of the body 110 of the cartridge 100 should be additionally vacuumized while mixing the powder and liquid components of bone cement, thereby making the procedure more complicated. Accordingly, when including the maintenance member 122 in the cartridge 100 as shown in FIG. 3, the internal space of the body 110 of the cartridge 100 is vacuumized before mixing the powder and liquid components of bone cement that have been inserted into the cartridge 100 and then the maintenance member 122 closes the internal space of the body 110 of the cartridge 100, thereby maintaining the vacuum of internal space thereof.

As such, the maintenance member 122 is retained during a process of shaking the cartridge 100 in opposite directions and mixing the powder and liquid component of bone cement by the mixing ball without additionally vacuumizing the internal space of the body 110 of the cartridge 100 after vacuumizing the internal space thereof. Accordingly, all configurations disclosed in the prior art may be employed as the maintenance member 122 if it can maintain the vacuum of the internal space of the body 110 of the cartridge 100 after vacuumizing the internal space thereof. Here, a configuration in which a check valve is disposed in the insertion hole 121a formed in the protruding member 121 of the first opening/closing means 120 may be employed as the embodiment of the maintenance member 122.

Figure 4:
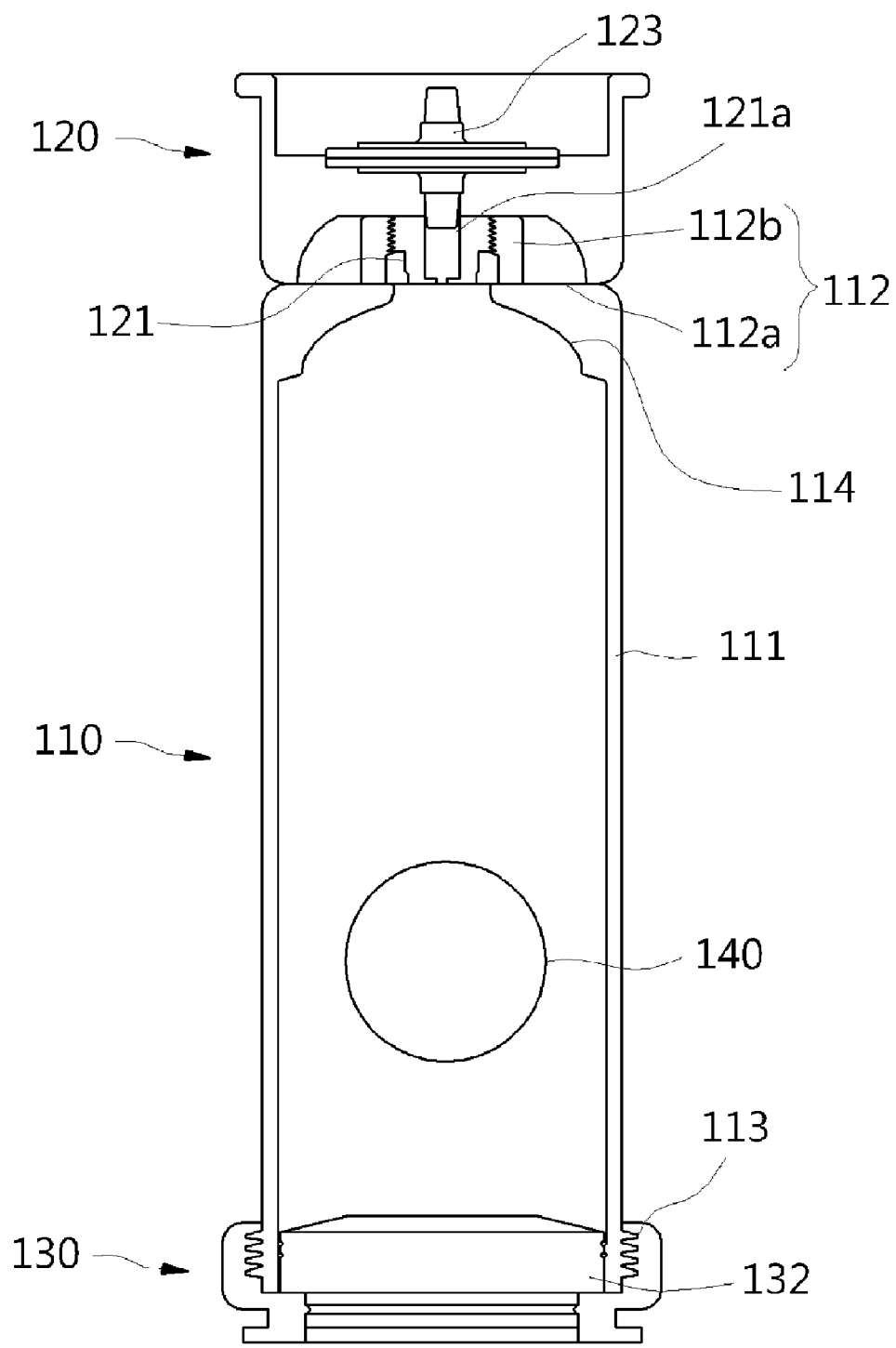
FIG. 4 is a cross-sectional view illustrating a cartridge for mixing and injecting bone cement according to a further embodiment of the present invention.
Figure 5:
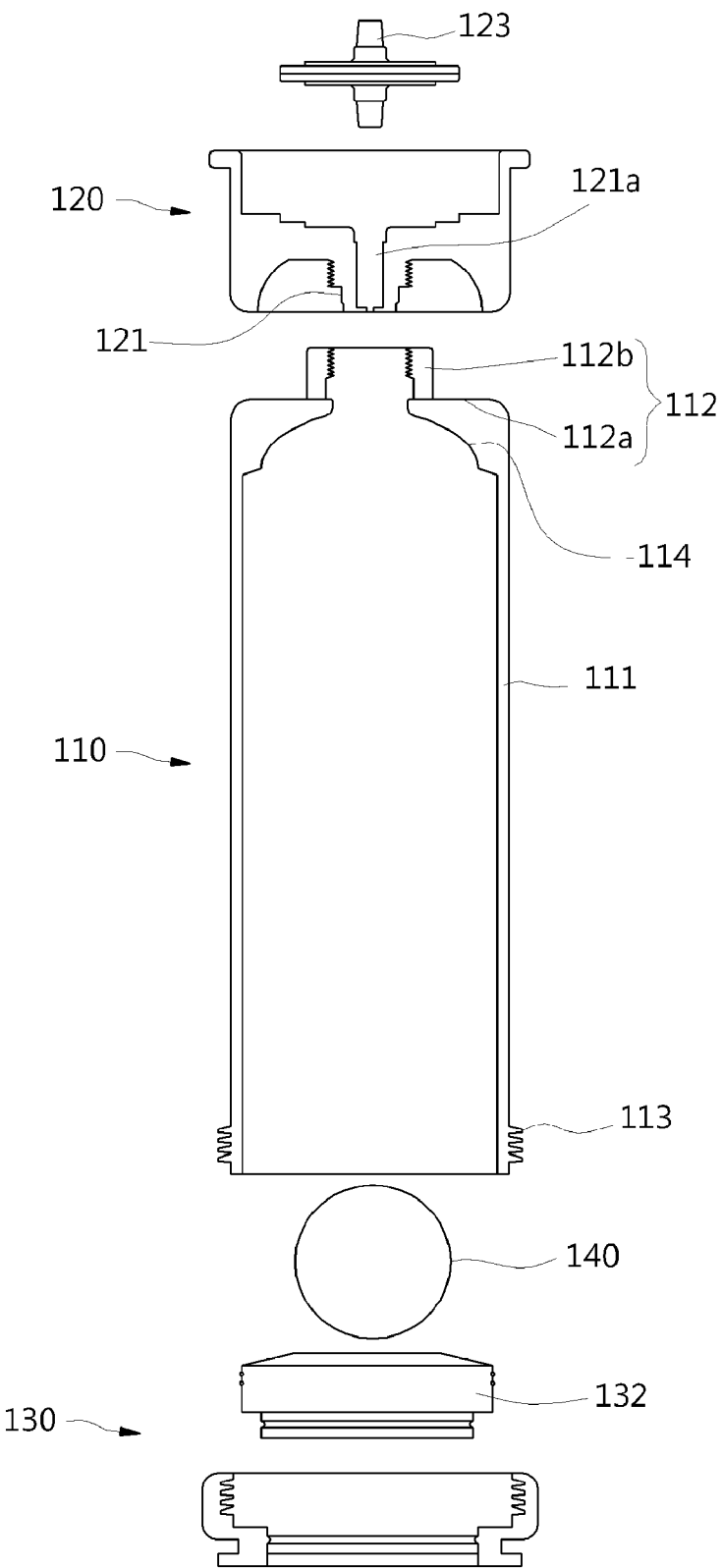
FIG. 5 is an exploded cross-sectional view illustrating the cartridge for mixing and injecting bone cement shown in FIG. 4.

FIGS. 4 and 5 are a cross-sectional view and an exploded cross-sectional view illustrating a cartridge 100 for mixing and injecting bone cement according to a further embodiment of the present invention.

As shown in FIGS. 4 and 5, the configuration of the cartridge 100 remains the same as the configuration of cartridge 100 of FIG. 2 except the structure of the first opening/closing means 120. Thus, the first opening/closing means 120 will be mainly described hereinafter.

Further, the first opening/closing means 120 of the cartridge 100 for mixing and injecting bone cement according to this embodiment of the present invention shown in FIGS. 4 and 5 has the same configuration as the first opening/closing means 120 shown in FIG. 2 except that a filter member 123 is further provided. Thus, other elements will refer to the above-mentioned description, so only the maintenance member 122 will be described hereinafter.

The filter member 123 is an element for eliminating odors that are discharged when vacuumizing the internal space of the body 110 of the cartridge 100. The filter member 123 eliminates strong odors generated by a volatile component of monomer, thereby solving a problem of health hazards to the operator such as nausea, dizziness, etc. during preparation of bone cement in the prior art. In other words, in the configurations of conventional cartridge of FIG. 1 and the cartridge of FIG. 2, when vacuumizing the internal space of the body 110 of the cartridge 100 by using a vacuum processing device such as a vacuum pump, the volatile component of monomer in the liquid component of bone cement is discharged therefrom all at once thereby generating strong odors causing extreme operator discomfort. On the other hand, when including the filter member 123 in the cartridge 100 as shown in FIGS. 4 and 5, it is possible to eliminate the strong odors that are generated by the volatile component of monomer in the liquid component of bone cement when vacuumizing the internal space of the body 110 of the cartridge 100. To this end, all configurations disclosed in the prior art may be employed as the filter member 123 if it can eliminate the odors that are discharged when vacuumizing the internal space of the body 110 of the cartridge 100. However, a configuration in which a vacuum filter member is disposed in the insertion hole 121a formed on the protruding member 121 of the first opening/closing means 120 may be employed as the embodiment of the filter member 123. In particular, the vacuum filter member may be a monomer evaporation filter.

Hereinafter, a configuration of the first opening/closing means 120 will be described more in detail with reference to FIGS. 6A and 6B. The first opening/closing means 120 shown in FIGS. 6A and 6B include the configuration of the first opening/closing means 120 shown in FIGS. 2 to 5. Accordingly, configurations of the protruding member 121 and the maintenance member 122 or the filter member 123 disposed in the insertion hole 121a are identical to the above-mentioned configurations so descriptions of elements will refer to the above-mentioned descriptions.

In other words, as described above, the shape of the first opening/closing means 120 is not limited if it can be coupled with the coupling means 112 of the body 110 so as to be opened and closed. However, the first opening/closing means 121 may have a structure in which the protruding member 121 that is inserted inside the coupling means 112 is coupled therewith, the maintenance member 122 is disposed in the insertion hole 121a formed in the protruding member 121 of the first opening/closing means 120 as shown in FIG. 3, and the filter member 123 is disposed in the insertion hole 121a formed in the protruding member 121 of the first opening/closing means 120 as shown in FIGS. 4 to 5. Particularly, FIGS. 6A and 6B show that the filter member 123 is disposed to a rear side of the maintenance member 122 that is disposed in the insertion hole 121a formed in the protruding member 121 of the first opening/closing means 120.

The cross-sectional view of FIG. 6A and the exploded cross-sectional view of FIG. 6B show that the first opening/closing means 120 is substantially formed in a shape of a cap in which the protruding member 121 is inserted inside an element that is to be sealed. Here, in order to have a structure that allows the filter member 123 to be easily disposed therein and allows the vacuum processing device to conveniently perform a vacuum process, the first opening/closing means 120 formed in the shape of the cap may be further provided with an external housing 124 that surrounds the protruding member 121 by being separated apart therefrom and forms a hollow space towards an upper side of the protruding member 121. Here, a depth of the hollow space may be larger than a height of the filter member 123.

Hereinafter, the configuration of the second opening/closing means 130 will be described more in detail with reference to views of FIGS. 7A and 7B. The configuration of the second opening/closing means 130 shown in FIGS. 7A and 7B is identical to that of the above-described second opening/closing means 130 so an O-ring and the plunger member 132 will be complementarily described below.

As described above, the second opening/closing means 130 includes the cylindrical hosing member 131 and the plunger member 132 detachably coupled with the first open end of the cylindrical hosing member 131. In particular, as shown in FIGS. 7A and 7B, the plunger member 132 may be formed in a shape in which at least one O-ring surrounds outer surfaces of an upper portion of the plunger member 132. As such, when the O-ring is provided on the outer surfaces of the plunger member 132, the plunger member 132 is tightly secured in an inner surface of the cylindrical member 111 that for Ls the internal space, and is moveable therein. Thus, it is possible to apply a proper pressure thereto when injecting bone cement using the cement gun 300.

Further, the plunger member 132 is a body having two or more disc portions having predetermined thicknesses and different diameters. In other words, as shown in FIG. 7B, the plunger member 132 is formed by a first disc portion, a second disc portion, a third disc portion, and a fourth disc portion. Here, the first disc portion is formed at the upper end of the plunger member 132 and has the greatest thickness and diameter. Further, the second disc portion, the third disc portion, and the fourth disc portion that have smaller thicknesses and diameters are sequentially formed on the center of the lower surface of the first disc portion. Particularly, the thickness and diameter of the second disc portion are equal to those of the fourth disc portion, and the thickness and diameter of the third disc portion positioned between the second and fourth disc portions are smaller than the thickness and diameter of the second and fourth disc portions. Thus, a groove is formed on a side surface of the plunger member 132 by the second to fourth disc portions. The groove is engaged with an annular protrusion formed on the inner surface of the cylindrical housing member 131.

Further, an upper surface of the first disc portion that forms the plunger member 132 may have a shape in which a center portion protrudes further than a peripheral portion thereof when considering a relationship with the mixing ball 140. In other words, when the upper surface of the plunger member 132 is formed in such a manner, it is predicted that the plunger member 132 will assist movement of the mixing ball 140 to a center of the internal space of the body 110 of the cartridge 100 when injecting bone cement.

As shown in FIG. 7A, while the cylindrical housing member 131 and the plunger member 132 are coupled with each other, the inner surface of the cylindrical housing member 131 downwardly extends so as to support the peripheral portion of the first disc portion that is not in surface-contact with the second disc portion of the plunger member 132, and forms the annular protrusion so as to be engaged with the groove that is formed on the side surface of the plunger member 132 by the second to fourth disc portions. Particularly, a lower end of the plunger member 132 is positioned more inside than a lower open end of the cylindrical housing member 131. In other words, the lower open end of the cylindrical housing member 131 is formed longer than a width of the lower end of the plunger member 132, thereby positioning the inner surface of the cylindrical housing member 131 to form a hollow space therein. Thus, the cement gun 300 is easily mounted on the cartridge 100 therethrough.

In such a manner, the second opening/closing means 130 is coupled with the second coupling means 113, the plunger member 132 is detachably coupled with the lower open end of the cylindrical housing member 131 and closes the second open end of the body 110 when not mounting the cement gun 300 on the cartridge. Further, as shown in FIG. 8, the plunger member 132 functions as an element for forcing bone cement into the injection tube 200 through the insertion portion 112b while moving inside the internal space of the body 110 of the cartridge 100.

Accordingly, the above-described structure according to the embodiment of the second opening/closing means 130 may be advantageous in injecting bone cement by mounting the cement gun 300 on the cartridge 100. In other words, it is possible to reduce pressure applied to the plunger member 132 by the mixing ball 140 when mixing bone cement in the cartridge 100, and easily force the plunger member 132 when the cement gun 300 pressurizes the plunger member 132.

Figure 9:
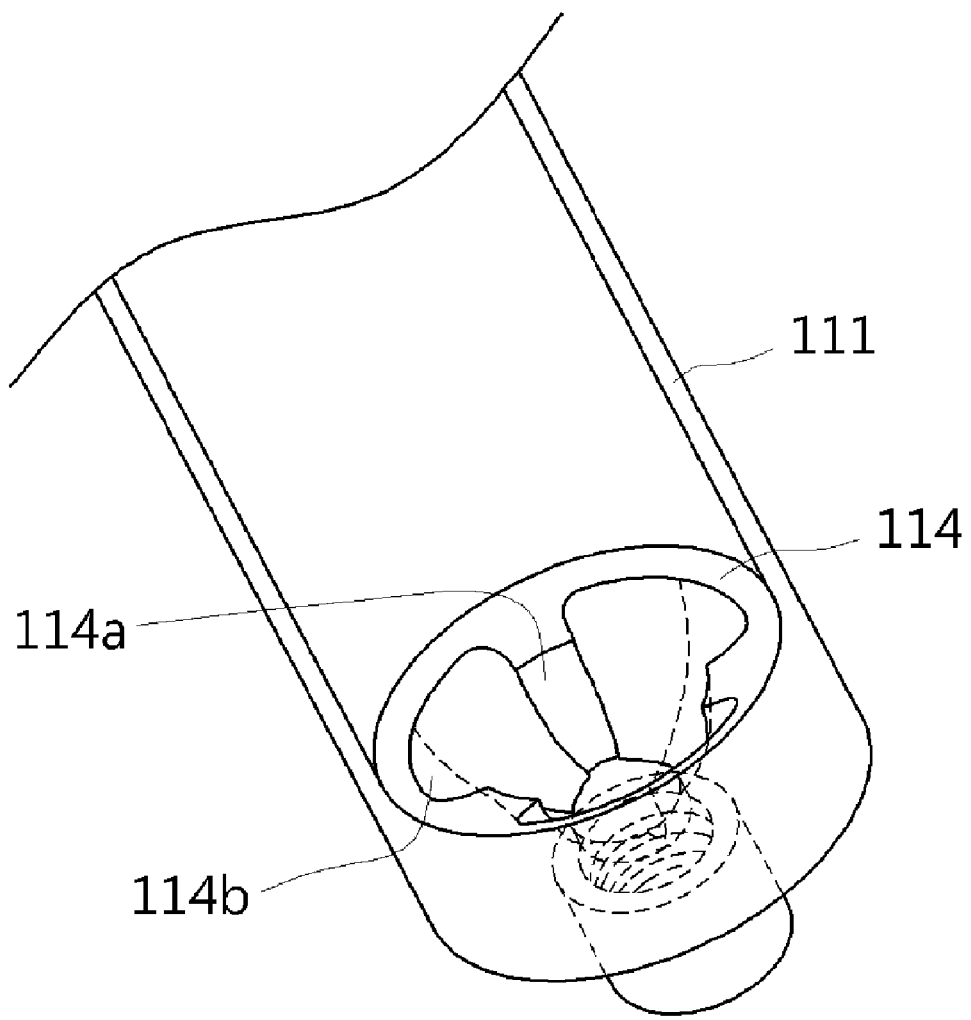
FIG. 9 is a perspective view illustrating an example of a mixing ball supporting portion shown in FIG. 8.

FIG. 8 is a schematic cross-sectional view illustrating that bone cement is discharged from the body 110 of the cartridge 100 for mixing and injecting bone cement of the present invention by the plunger member 132 without removing the mixing ball 140 from the body of the cartridge, and FIG. 9 is a perspective view illustrating a mixing ball supporting portion 114 illustrated in FIG. 8 according to an embodiment of present invention.

As shown in FIG. 8, in order to inject bone cement, which is obtained by uniformly mixing powder and liquid components of bone cement by using the mixing ball disposed inside the internal space of the body 110 of the cartridge 100, into the area to be treated without removing the mixing ball 140, bone cement should be discharged through the neck part 112b of the first coupling means 112 formed in a first open end of the body 110. Thus, it requires that the mixing ball 140 and/or the inner surface of the first coupling means 112, that is, inner surfaces of the neck part 112b and the shoulder part 112a of the first coupling means 112, be designed to prevent the mixing ball 140 from blocking an open end of the neck part 112b.

Accordingly, the mixing ball supporting portion 114 may be provided inside the first open end of the cylindrical member 111 and the first coupling means 112. As shown in FIG. 9, the mixing ball supporting portion 114 according to the embodiment of the present invention is forted as a dome shape based on a center of an opening of the neck part 112b inside the body 110. Further, two or more protruding portions 114a may be formed on a surface according to a distance between the protruding portion 114a and the opening of the neck part 112b, in which as the distance is reduced, the protruding portion 114a having a low height may be formed thereon, and as the distance is increased, the protruding portion 114a having a high height may be formed thereon. Thus, the mixing ball 140 is blocked by the protruding portion 114a and then the opening of the neck part 112b is open, so bone cement is discharged through a space 114b between the protruding portions 114a as shown in FIG. 8.

As shown in FIGS. 2 to 5, the cartridge 100 for mixing and injecting bone cement has a structure in which the first coupling means 112 and the second coupling means 113 formed in both open ends of the cylindrical member 111 of the body 112 are respectively and detachably coupled with the first opening/closing means 120 and the second opening/closing means 130 and thus forming a closed internal space where the mixing ball 140 is disposed therein. Accordingly, the second opening/closing means 130 is coupled with the body 110, and before the first opening/closing means 120 is coupled therewith, the powder and liquid component of bone cement are inserted into the internal space where the mixing ball 140 is disposed therein. Then, the first opening/closing means 120 is coupled with the first coupling means 112 and thus the powder and the liquid components of bone cement are uniformly mixed by the mixing ball 140 while shaking the cartridge 100 in opposite directions.

Next, a bone cement mixing and transferring system 1 of the present invention includes: the above-mentioned cartridge 100 for mixing the powder and liquid components of bone cement that has been inserted into the internal space of the body 110; an injection tube 200 coupled with the cartridge after removing the first opening/closing means 120 from the cartridge 100; and a cement gun 300 mounted to a rear side of the second opening/closing means 130 of the cartridge 100, the cement gun 300 applying pressure for injecting bone cement mixed in the cartridge 100 into the area to be treated via the injection tube 200.

Hereinafter, the bone cement mixing and transferring system 1 according to an embodiment of the present invention will be described with reference to FIG. 10.

Figure 10:
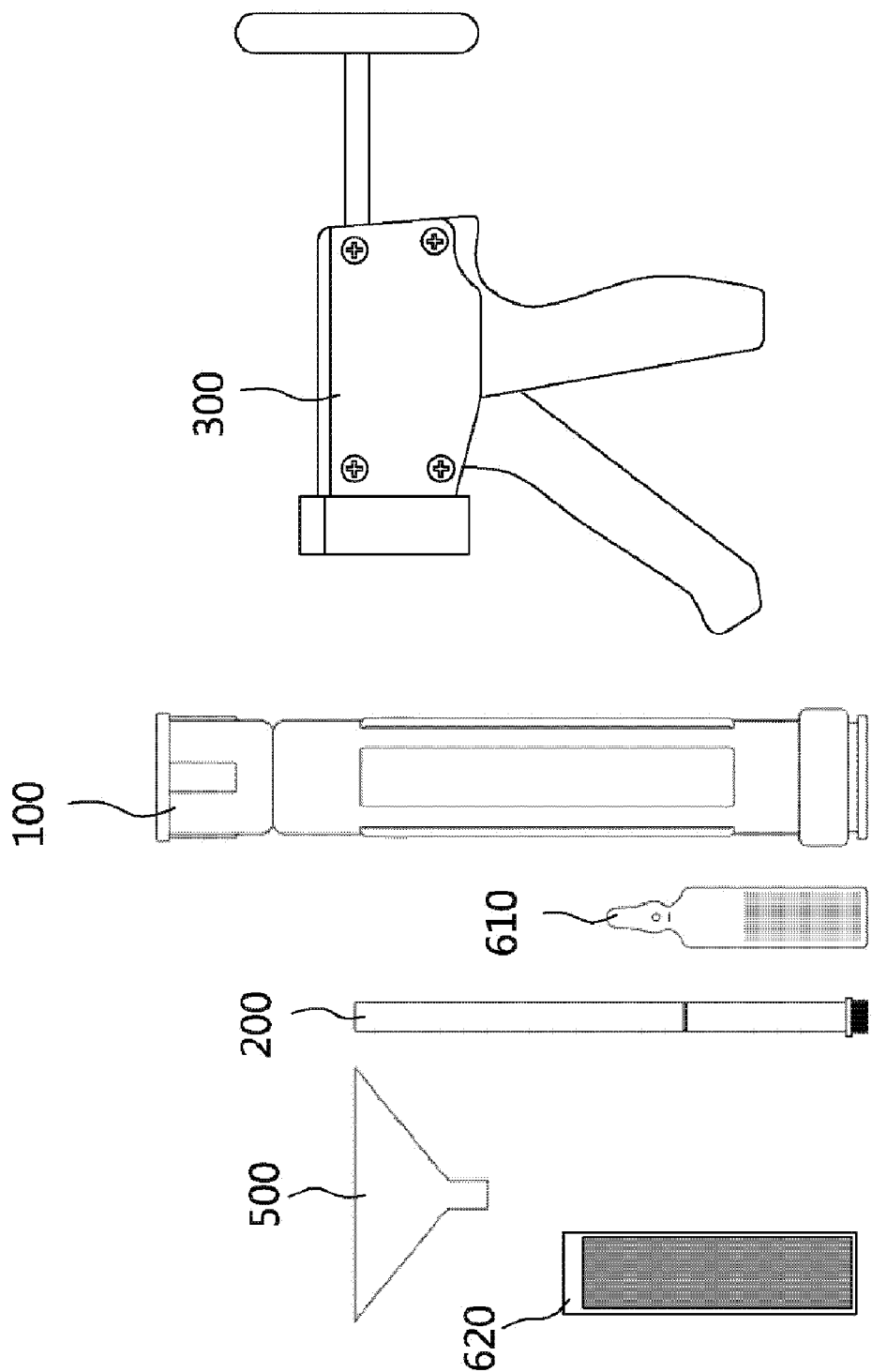
FIG. 10 is a schematic view illustrating a bone cement mixing and transferring system according to a further embodiment of the present invention.

As shown in FIG. 10, the bone cement mixing and transferring system 1 includes the cartridge 100 for mixing and injecting bone cement, the injection tube 200, the cement gun 300, the liquid component 610 of bone cement, and the powder component 620 of bone cement. Further, the vacuum processing device may be provided although that is not shown in the drawing. Further, an inserting tool 500 may be provided if necessary.

Here, the configuration of the cartridge 100 for mixing and injecting bone cement is identical to the above-mentioned cartridge 100, so detailed description thereof will be omitted.

The injection tube 200 has the same configuration as a conventional injection tube. However, there may be a difference in that a threaded portion that is coupled with the threaded portion formed in the inner surface of the neck part 112b is formed in a first end of the injection tube 200.

The cement gun 300 is advantageous in that a conventional cement gun may be employed as the cement gun 300 without changing a configuration thereof. Accordingly, the powder component 620 and liquid component 610 of bone cement are the same as those of the prior art so detailed description thereof will be omitted herein.

The vacuum processing device is used for vacuumizing the internal space of the body 110 of the cartridge 100. Particularly, the vacuum processing device may be used before mixing the powder and liquid components of bone cement that have been inserted into the internal space of the body 110 of the cartridge 100. Here, all configurations disclosed in the prior art may be employed as the vacuum processing device 400 if it can vacuumize the closed space by eliminating air therein. For example, the vacuum pump may be employed as the vacuum processing device 400.

Figure 12:
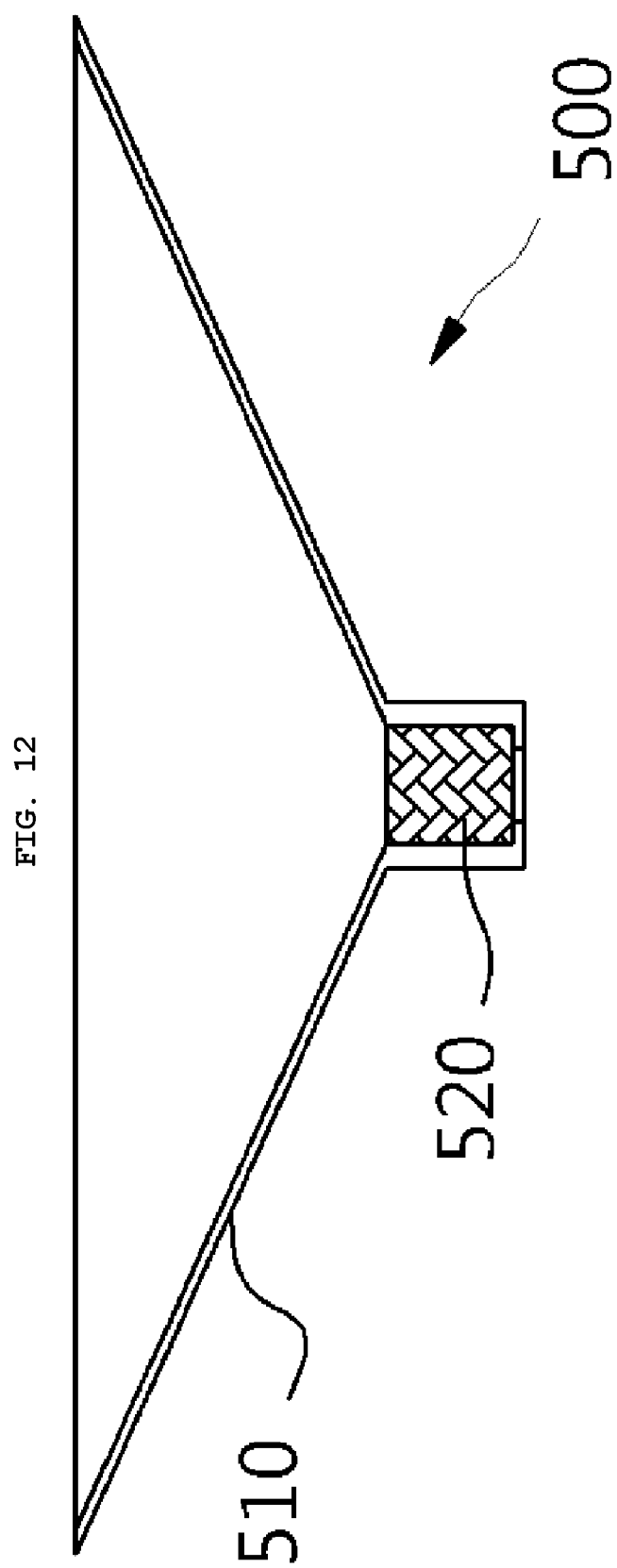
FIG. 12 is a cross-sectional view illustrating an example of an inserting tool shown in FIG. 10.

The inserting tool 500 is used when inserting the powder and liquid components of bone cement into the internal space of the body 110 of the cartridge 100. In the present invention, a conventional funnel 510 may be employed as the inserting tool 500. Further, as shown in FIG. 12, a filter 520 may be further provided in an end of the inserting tool 500 that comes into contact with the internal space of the body 110 of the cartridge 100. As such, when including the filter 520, it is possible to prevent impurities from being introduced into the cartridge by filtering pieces of glass that are generated when releasing a glass tube filled with the liquid component of bone cement. Further, the filter 520 of the inserting tool 500 is detachable therefrom, thereby removing the filter 520 when inserting the powder component 620 of bone cement into the cartridge 100 and mounting the filter 520 when inserting the liquid component 610 of bone cement thereto.

Hereinafter, a process of mixing and transferring bone cement to the area to be treated, performed by the bone cement mixing and transferring system shown in FIG. 10, will be described with reference to FIGS. 11A to 11F.

Figure 11A:
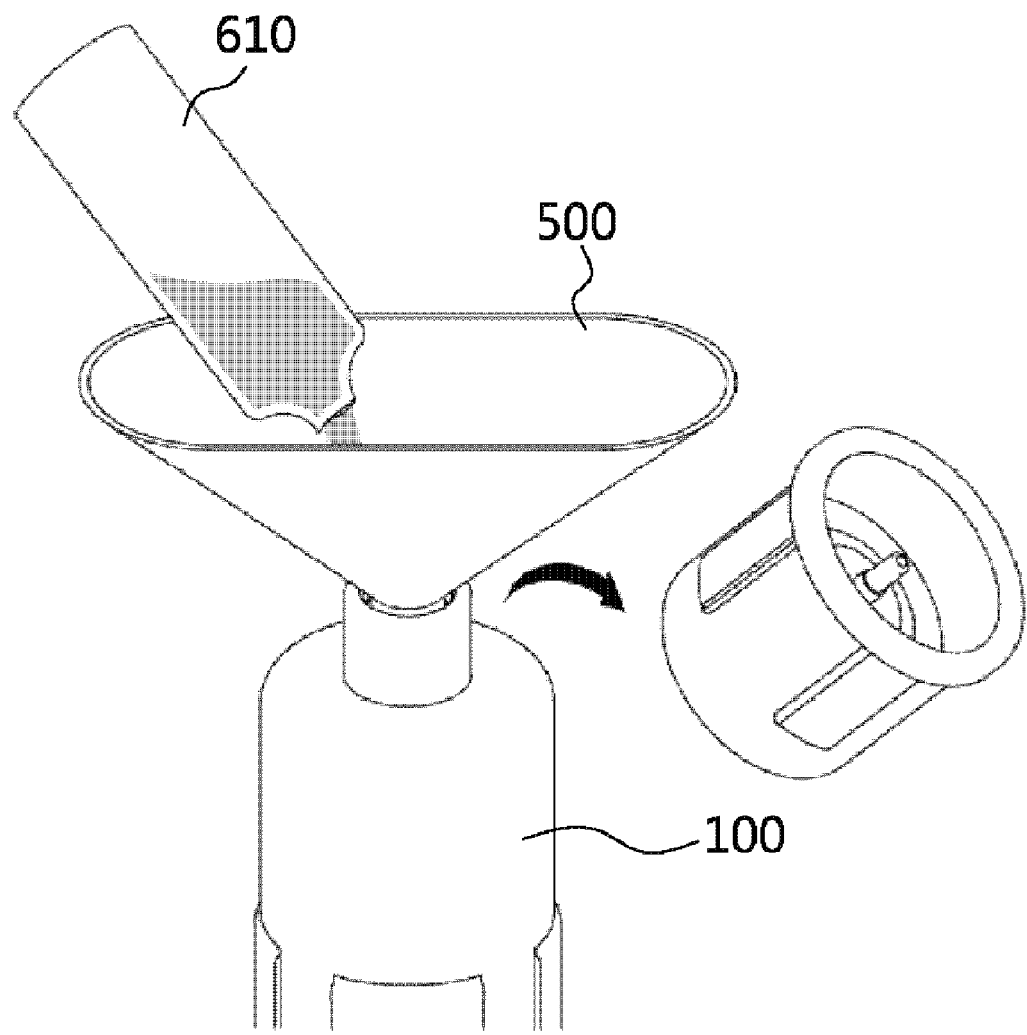
FIGS. 11A to 11F are schematic views illustrating a process of mixing and transferring bone cement to an area to be treated, performed by the bone cement mixing and transferring system illustrated in FIG. 10.
Figure 11B:
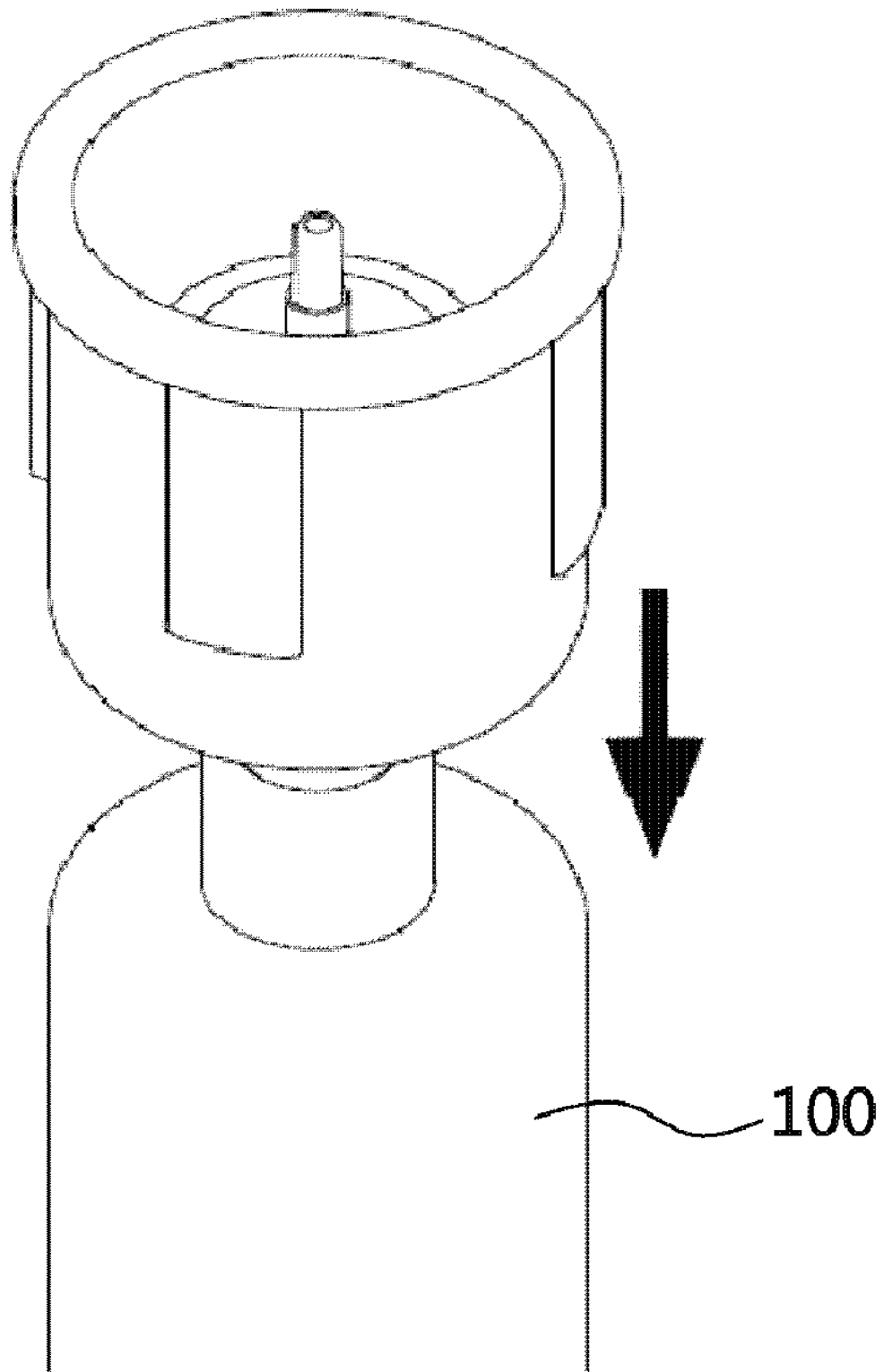
Figure 11C:
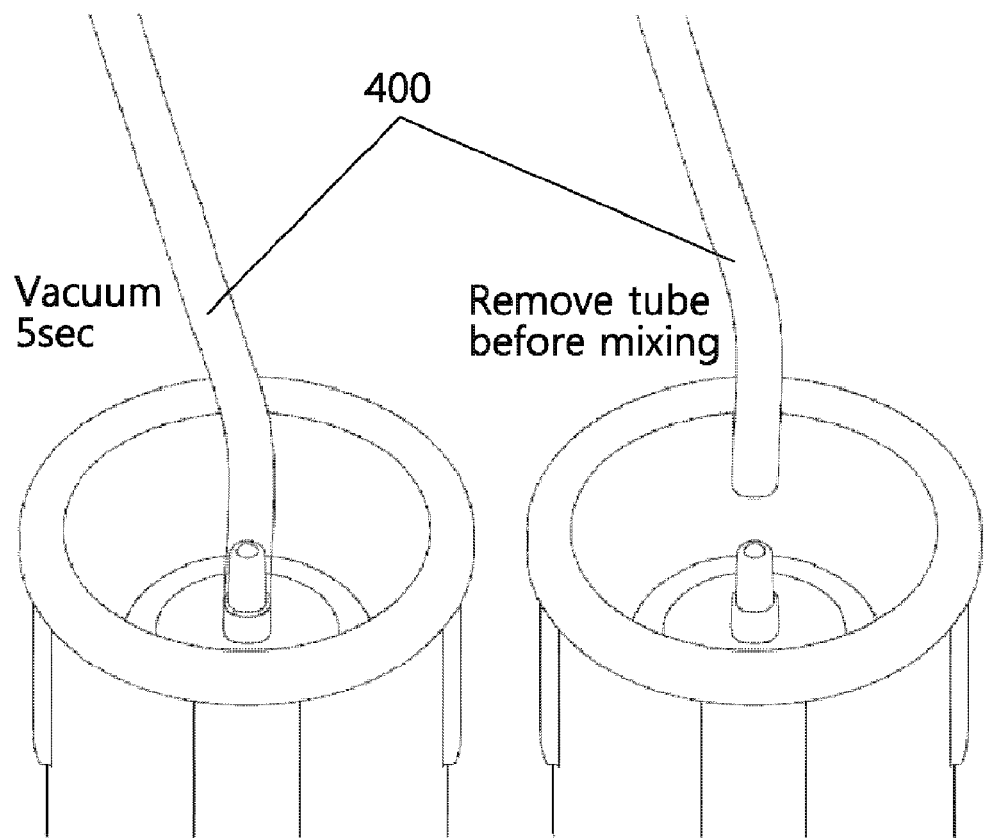
Figure 11D:
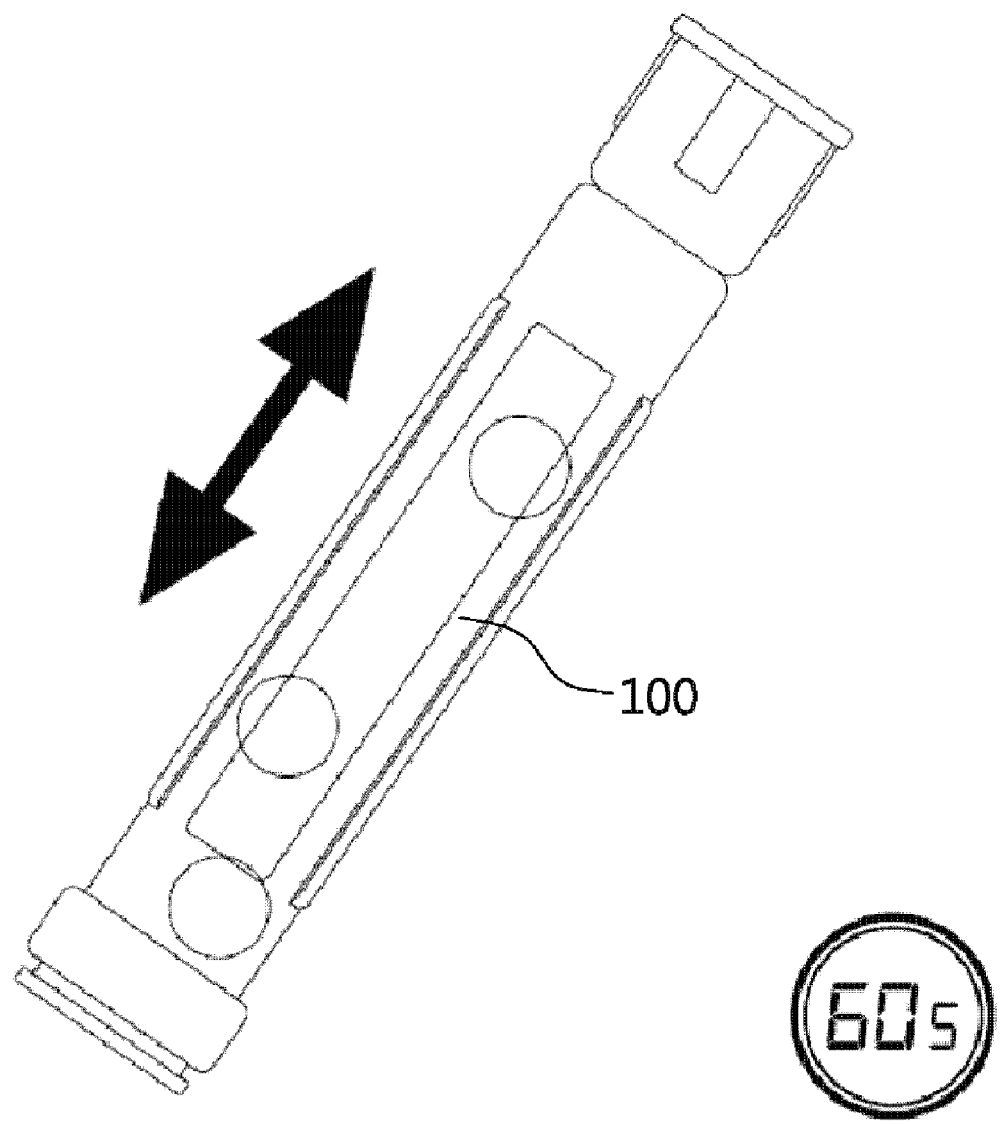
Figure 11E:
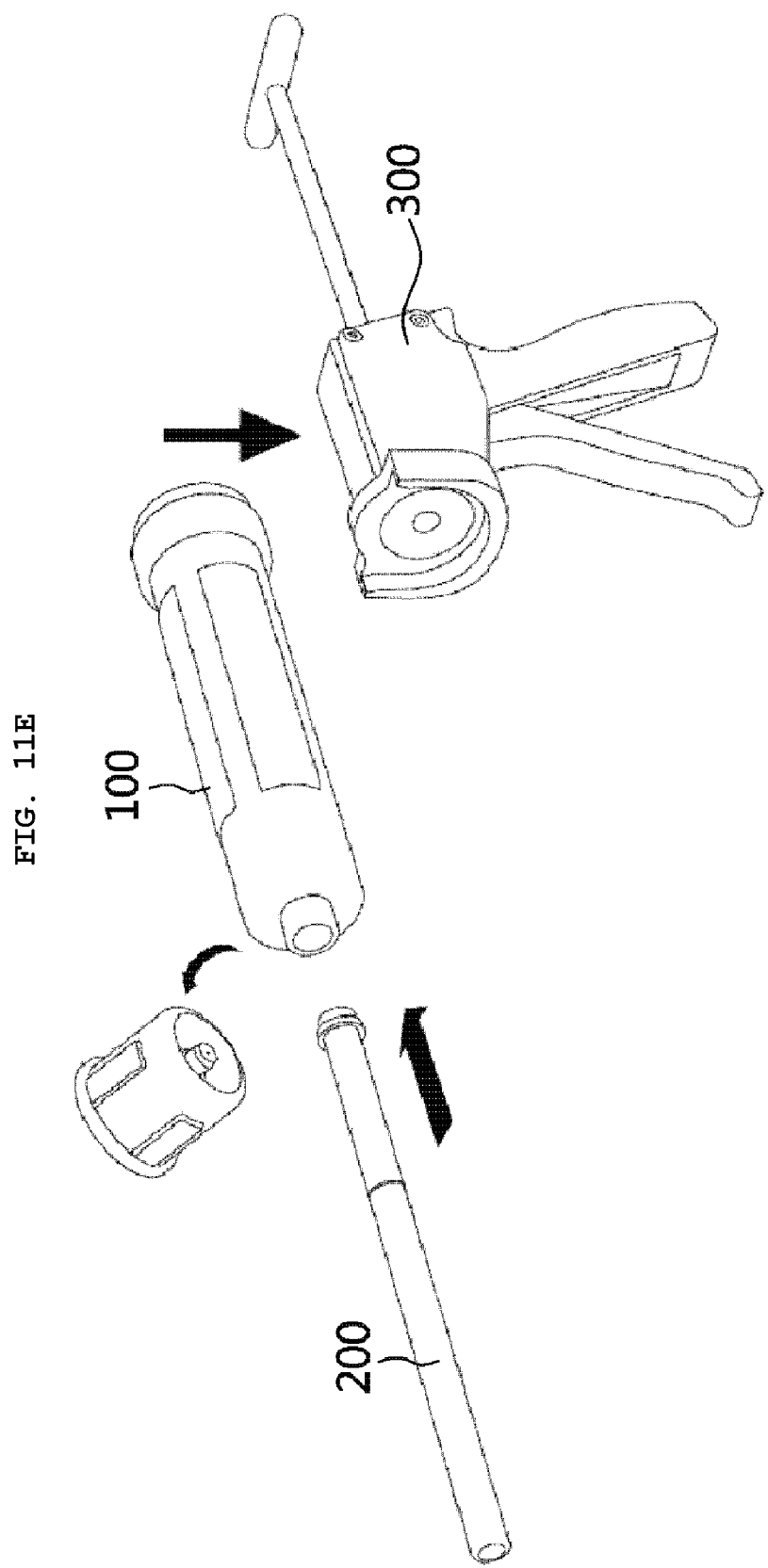
Figure 11F:
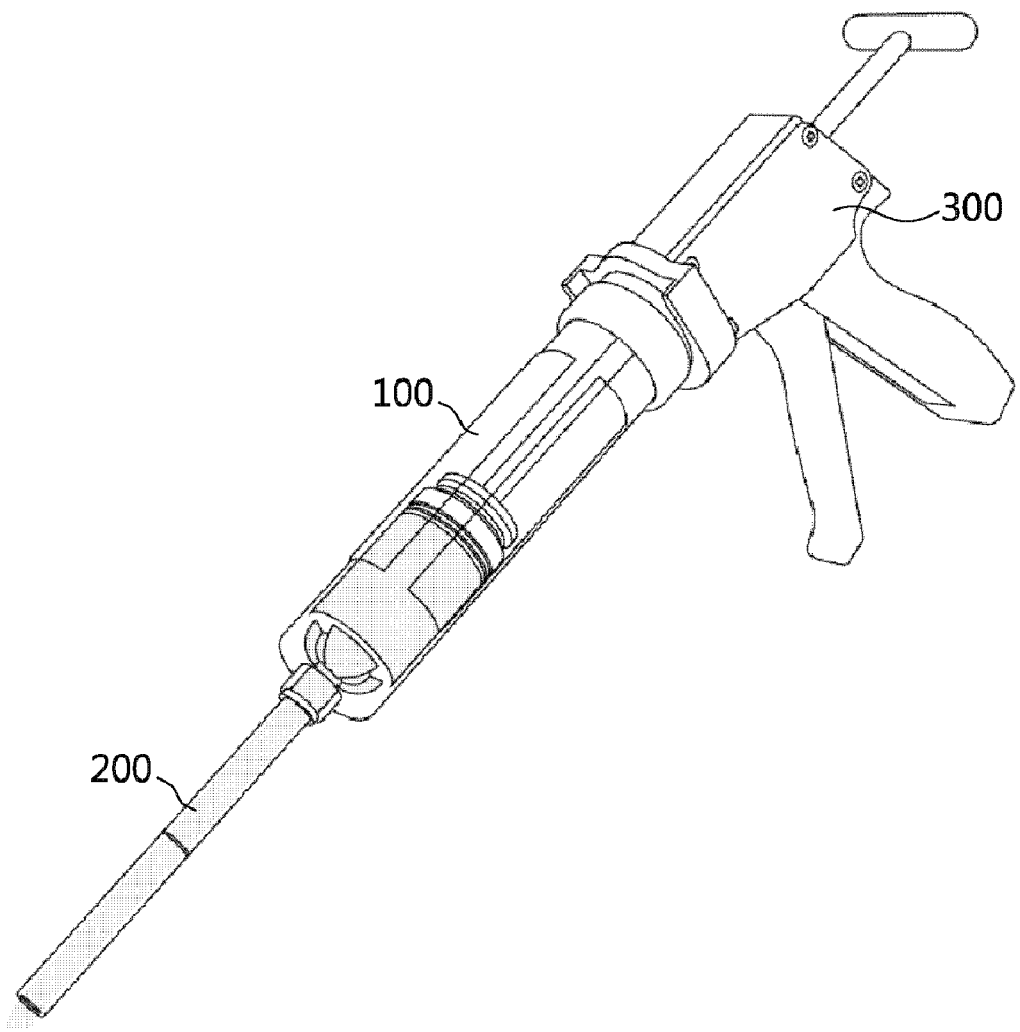

As shown in FIG. 11A, the powder component 620 and liquid component 610 of bone cement are inserted into the internal space of the body 110 of the cartridge 100 after the inserting tool 500 is disposed in the neck part 112b where the first opening/closing means 120 is removed therefrom. Then, as shown in FIG. 11B, the neck part 112b and the first opening/closing means 120 are coupled with each other and the internal space of the body 110 of the cartridge 100 is closed. Then, as shown in FIG. 11C, the internal space of the body 110 of the cartridge 100 is vacuumized by using the vacuum processing device 400 and the check valve is closed so as to maintain the vacuum of the internal space of the body 110 of the cartridge 100. Then, as shown in FIG. 11D, the powder and liquid component of bone cement that have been inserted into the cartridge 100 are uniformly mixed therein by shaking the cartridge 100 in opposite directions, thereby preparing bone cement. Then, as shown in FIG. 11E, the first opening/closing means 120 is removed from the cartridge 100 in which uniformly mixed bone cement is provided therein and then the injection tube 200 is coupled with the cartridge 100 and then the cement gun 300 is mounted to the rear side of the second opening/closing means 130. Then, as shown in FIG. 11F, bone cement 600 is injected into the area to be treated by operating the cement gun 300.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A cartridge for mixing and injecting bone cement, the cartridge comprising:
   a body including a cylindrical member having a square cross-section in a lengthwise direction thereof, the cylindrical member having a first open end through which the bone cement is discharged and a second open end opposite to the first open end;
a first coupler provided at a first open end of the cylindrical member;
a second coupler provided at a second open end of the cylindrical member;
a first opening/closing member detachably coupled with the first coupler;
a second opening/closing member detachably coupled with the second coupler; and
at least one mixing ball provided in an internal space of the body; and
a mixing ball supporting portion provided inside the first open end of the cylindrical member and the first coupler, the mixing ball supporting portion formed as a dome shape.

2. The cartridge of claim 1, wherein the first coupler is provided with:
a shoulder part provided at a first open end of the cylindrical member, the shoulder part extending therefrom; and
a neck part cylindrically protruding from a center of the first open end of the cylindrical member by perpendicularly extending from the shoulder part.

3. The cartridge of claim 1, wherein the first opening/closing member is provided with a protruding member that is inserted into the first coupler and is coupled with the first coupler, and the protruding member has an insertion hole.

4. The cartridge of claim 1, wherein the second coupler is provided with a threaded portion integrally formed on an outer surface of the second open end of the cylindrical member.

5. The cartridge of claim 1, wherein the second opening/closing member is provided with:
a cylindrical housing member that surrounds an outer surface of the second coupler and is coupled with the second coupler, the cylindrical housing member having an annular protrusion formed on the inner surface of the cylindrical housing member; and
a plunger member detachably coupled with a first open end of the cylindrical housing member, the plunger member having a groove formed on a side surface of the plunger member to be engaged with the annular protrusion of the cylindrical housing member,
wherein a lower open end of the cylindrical housing member is formed longer than the lower end of the plunger member to form a hollow space in the cylindrical housing member.

6. The cartridge of claim 5, wherein when the second opening/closing member is coupled with the second coupler, the cylindrical member is inserted between the cylindrical housing member and the plunger member.

7. The cartridge of claim 5, wherein a first end of the plunger member is detachably coupled with the cylindrical housing member, and a second end of the plunger member is provided with an O-ring.

8. The cartridge of claim 3, further comprising:
a maintenance member maintaining a vacuum of the internal space of the body after the internal space of the body is vacuumized, the maintenance member disposed in the insertion hole formed in the protruding member.

9. The cartridge of claim 8, wherein the maintenance member is a check valve provided in the first opening/closing member.

10. The cartridge of claim 1, further comprising:
a filter member eliminating odors that are discharged when vacuumizing the internal space of the body of the cartridge, the filter member disposed in the insertion hole formed in the protruding member and to a rear side of the maintenance member,
wherein the first opening/closing member is formed in the shape of a cap;
the first opening/closing member is further provided with an external housing hat surrounds the protruding member by being separated apart therefrom and forms a hollow space towards an upper side of the protruding member;
a depth of the hollow space is larger than a height of the filter member.

11. A bone cement mixing and transferring system, comprising:
the cartridge of claim 1, the cartridge having powder and liquid components of bone cement inserted into the internal space thereof and mixing the powder and liquid components therein;
an injection tube coupled with the cartridge after removing the first opening/closing member from the cartridge; and
a cement gun mounted to a rear side of the second opening/closing member of the cartridge, the cement gun applying pressure for injecting bone cement mixed in the cartridge into an area to be treated via the injection tube.

12. The system of claim 11, further comprising:
a vacuum processing device performing a vacuum process of vacuumizing the internal space of the body of the cartridge.

13. The system of claim 12, wherein the vacuum processing device is used before mixing the powder and liquid components of bone cement that have been inserted into the internal space of the body of the cartridge.

14. The system of claim 11, further comprising:
an inserting tool used when inserting the powder and liquid components of bone cement into the internal space of the body of the cartridge.

15. The system of claim 14, wherein the inserting tool includes a filter provided in an end of the inserting tool that comes into contact with the internal space of the body of the cartridge.

16. The system of claim 11, wherein the powder and liquid components of bone cement that have been inserted into the internal space of the body of the cartridge are mixed therein by shaking the cartridge in lengthwise directions thereof.

17. A bone cement mixing and transferring system, comprising:
the cartridge of claim 8, the cartridge having powder and liquid components of bone cement inserted into the internal space thereof and mixing the powder and liquid components therein;
an injection tube coupled with the cartridge after removing the first opening/closing member from the cartridge; and
a cement gun mounted to a rear side of the second opening/closing member of the cartridge, the cement gun applying pressure for injecting bone cement mixed in the cartridge into an area to be treated via the injection tube.

18. A bone cement mixing and transferring system, comprising:

the cartridge of claim 10, the cartridge having powder and liquid components of bone cement inserted into the internal space thereof and mixing the powder and liquid components therein;

an injection tube coupled with the cartridge after removing the first opening/closing member from the cartridge; and a cement gun mounted to a rear side of the second opening/closing member of the cartridge, the cement gun applying pressure for injecting bone cement mixed in the cartridge into an area to be treated via the injection tube.

19. A bone cement mixing and transferring system, comprising:

the cartridge of claim 1, the cartridge having powder and liquid components of bone cement inserted into the internal space thereof and mixing the powder and liquid components therein;

an injection tube coupled with the cartridge after removing the first opening/closing member from the cartridge; and a cement gun mounted to a rear side of the second opening/closing member of the cartridge, the cement gun applying pressure for injecting bone cement mixed in the cartridge into an area to be treated via the injection tube.

20. The cartridge of claim 2, wherein the mixing ball supporting portion has protruding portions formed protruding from a surface of the mixing ball supporting portion; and a height of each of the protruding portions is decreased in the direction to the opening of the neck.

* * * * *